(12) United States Patent
Kerek

(10) Patent No.: US 7,750,114 B2
(45) Date of Patent: Jul. 6, 2010

(54) PEPTIDES HAVING A HIGH CYSTEINE CONTENT

(76) Inventor: Franz Kerek, Guardinistrasse 30, 81375 Munich (DE)

( * ) Notice: Subject to any disclaimer, the term of this patent is extended or adjusted under 35 U.S.C. 154(b) by 1116 days.

(21) Appl. No.: 10/540,305

(22) PCT Filed: Dec. 20, 2003

(86) PCT No.: PCT/DE03/04228

§ 371 (c)(1),
(2), (4) Date: Dec. 19, 2005

(87) PCT Pub. No.: WO2004/058813

PCT Pub. Date: Jul. 15, 2004

(65) Prior Publication Data

US 2006/0183679 A1 Aug. 17, 2006

(30) Foreign Application Priority Data

Dec. 21, 2002 (DE) .............................. 102 60 537

(51) Int. Cl.
A61K 47/42 (2006.01)
A61K 38/00 (2006.01)

(52) U.S. Cl. .................. 530/323; 514/2; 424/278.1

(58) Field of Classification Search ................. None
See application file for complete search history.

(56) References Cited

U.S. PATENT DOCUMENTS 7,125,687 B1 * 10/2006 Curtis et al. ................. 435/69.1
7,309,759 B2 * 12/2007 Krieger et al. .............. 530/300

FOREIGN PATENT DOCUMENTS

DE 4208923 9/1993
WO WO 02/22159 3/2002

OTHER PUBLICATIONS

Evans et al. (1989) Cellular responses to Pyrularia thionin are mediated by Ca2+ influx and phospholipase A2 activation and are inhibited by thionin tyrosine iodination, Proc. Natl. Acad. Sci. U S A., vol. 89, No. 15, pp. 5849-5853.*

Hashimoto et al. (2002) Neurotoxic mechanisms triggered by Alzheimer's disease-linked mutant M146L presenilin 1: involvement of NO synthase via a novel pertussis toxin target, J. Neurochem., vol. 80, No. 3, pp. 426-437.*
MacKay et al. (1993) Complete amino acid sequences of five dimeric and four monomeric forms of metallothionein from the edible mussel Mytilus edulis, Eur. J. Biochem., vol. 218, No. 1, pp. 183-194.*
Sauve et al. (1985) Gilles Sauve' et al, Backbone-modified oligopeptidic bioregulators. The synthesis and configuration of thioamide, amidoxime, cyanoamidine, and amidrazone analogs of the chemotactic peptide N-formyl-methionyl-leucyl-phenylalanine (f-Met-Leu-Phe-OR), Can. J. Chem., vol. 63, pp. 3089-3101.*
Andresen et al. (1992) The identification of leaf thionin as one of the main jasmonate-induced proteins of barley (Hordeum vulgare), Plant Mol. Biol., vol. 19, No. 2, pp. 193-204.*
Comeglio et al. (2001) Detection of six novel FBN1 mutations in British patients affected by Marfan syndrome, Human Mutation, (Mutation in Brief # 438), pp. 1-6.*
Kim et al. (2005) Oligomerization and multimerization are critical for angiopoietin-1 to bind and phosphorylate Tie2, J. Biol. Chem., vol. 280, No. 20, pp. 20126-20131.*
"Structural Characterization of Hellethionins from Helleborus purpurascens" By Alexander G. Milbradt et al. / Biochemistry 2003, vol. 42, No. 8 / pp. 2404-2411.
Francisco Garcia-Olmedo et al., "Plant Defense Peptides" Biopolymers (Peptide Science), vol. 47, 1998, pp. 179-491.
"Pyrularia Thionin" www.nchi.nlm.nih.gov/entrez/viewer_fcgi?val=82024.

* cited by examiner

Primary Examiner—Anand U Desai
Assistant Examiner—Samuel W Liu
(74) Attorney, Agent, or Firm—J.C. Patents

(57) ABSTRACT

The invention relates to cysteine containing peptides of the structure XXCCXXXXXXXCXXXCXXXXXQXX-CXXXCXCXXXXXXCXXXXX, of the structure XXC-CXXXXXXXCXXXCXXXXXXXCXXXCXCXXXX-TXXCXXXXXX and of the structure XXCCXXXXXX-CXXXCXXXXXXXXXCXXXCXCXXXXXXXCXX-XXXX, wherein X, independently of one another, represents any naturally occurring amino acid, as well as to nucleic acid sequences encoding said peptides, to vectors comprising said sequences, as well as to pharmaceutical compositions containing said peptides and their use as pharmaceutics, particularly for the treatment of cancers.

10 Claims, 2 Drawing Sheets

SEQUENCE LISTING

<160> NUMBER OF SEQ ID NOS: 16

<210> SEQ ID NO 1
<211> LENGTH: 46
<212> TYPE: PRT
<213> ORGANISM: Helleborus purpurascens

<400> SEQUENCE: 1

Lys Ser Cys Cys Arg Asn Thr Leu Gly Arg Asn Cys Tyr Asn Gly Cys
1               5                   10                  15

Arg Phe Thr Gly Gly Ser Gln Pro Thr Cys Gly Arg Leu Cys Asp Cys
            20                  25                  30

Ile His Val Thr Thr Thr Thr Cys Pro Ser Ser His Pro Ser
        35                  40                  45

<210> SEQ ID NO 2
<211> LENGTH: 46
<212> TYPE: PRT
<213> ORGANISM: Helleborus purpurascens

<400> SEQUENCE: 2

Lys Ser Cys Cys Arg Asn Thr Leu Gly Arg Asn Cys Tyr Asn Ala Cys
1               5                   10                  15

Arg Phe Thr Gly Gly Ser Gln Pro Thr Cys Gly Arg Leu Cys Asp Cys
            20                  25                  30

Ile His Val Thr Thr Thr Thr Cys Pro Ser Ser His Pro Ser
        35                  40                  45

<210> SEQ ID NO 3
<211> LENGTH: 46
<212> TYPE: PRT
<213> ORGANISM: Helleborus purpurascens

<400> SEQUENCE: 3

Lys Ser Cys Cys Arg Asn Thr Leu Ala Arg Asn Cys Tyr Asn Ala Cys
1               5                   10                  15

Arg Phe Thr Gly Gly Ser Gln Pro Thr Cys Gly Arg Leu Cys Asp Cys
            20                  25                  30

Ile His Val Thr Thr Thr Thr Cys Pro Ser Ser His Pro Ser
        35                  40                  45

<210> SEQ ID NO 4
<211> LENGTH: 46
<212> TYPE: PRT
<213> ORGANISM: Helleborus purpurascens

<400> SEQUENCE: 4

Lys Ser Cys Cys Arg Asn Thr Leu Gly Arg Asn Cys Tyr Asn Ala Cys
1               5                   10                  15

Arg Leu Pro Gly Thr Pro Gln Pro Thr Cys Ala Thr Leu Cys Asp Cys
            20                  25                  30

Ile His Val Thr Thr Pro Thr Cys Pro Ser Ser His Pro Arg
        35                  40                  45

<210> SEQ ID NO 5
<211> LENGTH: 46
<212> TYPE: PRT
<213> ORGANISM: Helleborus purpurascens

<400> SEQUENCE: 5

```
Lys Ser Cys Cys Arg Asn Thr Leu Ala Arg Asn Cys Tyr Asn Ala Cys
1               5                   10                  15

Arg Phe Thr Gly Thr Ser Gln Pro Tyr Cys Ala Arg Leu Cys Asp Cys
            20                  25                  30

Ile His Val Thr Thr Pro Thr Cys Pro Ser Ser His Pro Arg
            35                  40                  45
```

<210> SEQ ID NO 6
<211> LENGTH: 46
<212> TYPE: PRT
<213> ORGANISM: Helleborus purpurascens

<400> SEQUENCE: 6

```
Lys Ser Cys Cys Arg Asn Thr Leu Ala Arg Asn Cys Tyr Asn Ala Cys
1               5                   10                  15

Arg Phe Thr Gly Gly Ser Gln Pro Thr Cys Ala Thr Leu Cys Asp Cys
            20                  25                  30

Ile His Val Thr Thr Pro Thr Cys Pro Ser Ser His Pro Arg
            35                  40                  45
```

<210> SEQ ID NO 7
<211> LENGTH: 46
<212> TYPE: PRT
<213> ORGANISM: Helleborus purpurascens

<400> SEQUENCE: 7

```
Lys Ser Cys Cys Arg Asn Thr Leu Ala Arg Asn Cys Tyr Asn Val Cys
1               5                   10                  15

Arg Phe Gly Gly Gly Ser Gln Ala Tyr Cys Ala Arg Phe Cys Asp Cys
            20                  25                  30

Ile His Val Thr Thr Ser Thr Cys Pro Ser Ser His Pro Ser
            35                  40                  45
```

<210> SEQ ID NO 8
<211> LENGTH: 46
<212> TYPE: PRT
<213> ORGANISM: Helleborus purpurascens

<400> SEQUENCE: 8

```
Lys Ser Cys Cys Arg Asn Thr Leu Gly Arg Asn Cys Tyr Asn Ala Cys
1               5                   10                  15

Arg Leu Thr Gly Thr Ser Gln Ala Thr Cys Ala Thr Leu Cys Asp Cys
            20                  25                  30

Ile His Val Thr Ala Thr Thr Cys Arg Pro Pro Tyr Pro Ser
            35                  40                  45
```

<210> SEQ ID NO 9
<211> LENGTH: 46
<212> TYPE: PRT
<213> ORGANISM: Helleborus purpurascens

<400> SEQUENCE: 9

```
Lys Ser Cys Cys Arg Asn Thr Leu Ala Arg Asn Cys Tyr Asn Ala Cys
1               5                   10                  15

Arg Phe Thr Gly Gly Ser Gln Pro Thr Cys Gly Ile Leu Cys Asp Cys
            20                  25                  30

Ile His Val Thr Thr Thr Thr Cys Pro Ser Ser His Pro Ser
            35                  40                  45
```

<210> SEQ ID NO 10
<211> LENGTH: 48
<212> TYPE: PRT
<213> ORGANISM: Helleborus purpurascens

<400> SEQUENCE: 10

Lys Ser Cys Cys Arg Asn Thr Leu Gly Arg Asn Cys Tyr Ala Ala Cys
1               5                   10                  15

Arg Leu Thr Gly Leu Phe Ser Gln Glu Gln Cys Ala Arg Leu Cys Asp
            20                  25                  30

Cys Ile Thr Val Thr Thr Pro Thr Pro Cys Pro Arg Thr His Pro Ser
        35                  40                  45

<210> SEQ ID NO 11
<211> LENGTH: 48
<212> TYPE: PRT
<213> ORGANISM: Helleborus purpurascens

<400> SEQUENCE: 11

Lys Ser Cys Cys Arg Asn Thr Leu Gly Arg Asn Cys Tyr Ala Ala Cys
1               5                   10                  15

Arg Leu Thr Gly Thr Phe Ser Gln Glu Gln Cys Ala Arg Leu Cys Asp
            20                  25                  30

Cys Ile Thr Val Thr Thr Pro Thr Pro Cys Pro Arg Thr His Pro Ser
        35                  40                  45

<210> SEQ ID NO 12
<211> LENGTH: 46
<212> TYPE: PRT
<213> ORGANISM: Helleborus purpurascens
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(22)
<223> OTHER INFORMATION: Xaa can be any naturally occurring amino acid
<220> FEATURE:
<221> NAME/KEY: misc_feature
<222> LOCATION: (24)..(25)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(39)
<223> OTHER INFORMATION: Xaa can be any naturally occurring amino acid
<220> FEATURE:
<221> NAME/KEY: misc_feature
<222> LOCATION: (41)..(46)
<223> OTHER INFORMATION: Xaa can be any naturally occurring amino acid

<400> SEQUENCE: 12

Xaa Xaa Cys Cys Xaa Xaa Xaa Xaa Xaa Xaa Xaa Cys Xaa Xaa Xaa Cys
1               5                   10                  15

Xaa Xaa Xaa Xaa Xaa Xaa Gln Xaa Xaa Cys Xaa Xaa Xaa Cys Xaa Cys
            20                  25                  30

Xaa Xaa Xaa Xaa Xaa Xaa Xaa Cys Xaa Xaa Xaa Xaa Xaa Xaa
        35                  40                  45

<210> SEQ ID NO 13
<211> LENGTH: 46
<212> TYPE: PRT
<213> ORGANISM: Helleborus purpurascens
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(25)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(36)
<223> OTHER INFORMATION: Xaa can be any naturally occurring amino acid
<220> FEATURE:
<221> NAME/KEY: misc_feature
<222> LOCATION: (38)..(39)
<223> OTHER INFORMATION: Xaa can be any naturally occurring amino acid
<220> FEATURE:
<221> NAME/KEY: misc_feature
<222> LOCATION: (41)..(46)
<223> OTHER INFORMATION: Xaa can be any naturally occurring amino acid

<400> SEQUENCE: 13

Xaa Xaa Cys Cys Xaa Xaa Xaa Xaa Xaa Xaa Xaa Cys Xaa Xaa Xaa Cys
1               5                   10                  15

Xaa Xaa Xaa Xaa Xaa Xaa Xaa Xaa Xaa Cys Xaa Xaa Xaa Cys Xaa Cys
            20                  25                  30

Xaa Xaa Xaa Xaa Thr Xaa Xaa Cys Xaa Xaa Xaa Xaa Xaa Xaa
        35                  40                  45

<210> SEQ ID NO 14
<211> LENGTH: 48
<212> TYPE: PRT
<213> ORGANISM: Helleborus purpurascens
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature

```
<222> LOCATION: (17)..(26)
<223> OTHER INFORMATION: Xaa can be any naturally occurring amino acid
<220> FEATURE:
<221> NAME/KEY: misc_feature
<222> LOCATION: (28)..(30)
<223> OTHER INFORMATION: Xaa can be any naturally occurring amino acid
<220> FEATURE:
<221> NAME/KEY: misc_feature
<222> LOCATION: (32)..(32)
<223> OTHER INFORMATION: Xaa can be any naturally occurring amino acid
<220> FEATURE:
<221> NAME/KEY: misc_feature
<222> LOCATION: (34)..(41)
<223> OTHER INFORMATION: Xaa can be any naturally occurring amino acid
<220> FEATURE:
<221> NAME/KEY: misc_feature
<222> LOCATION: (43)..(48)
<223> OTHER INFORMATION: Xaa can be any naturally occurring amino acid

<400> SEQUENCE: 14

Xaa Xaa Cys Cys Xaa Xaa Xaa Xaa Xaa Xaa Xaa Cys Xaa Xaa Xaa Cys
1               5                   10                  15

Xaa Xaa Xaa Xaa Xaa Xaa Xaa Xaa Xaa Xaa Cys Xaa Xaa Xaa Cys Xaa
            20                  25                  30

Cys Xaa Xaa Xaa Xaa Xaa Xaa Xaa Cys Xaa Xaa Xaa Xaa Xaa Xaa
        35                  40                  45

<210> SEQ ID NO 15
<211> LENGTH: 47
<212> TYPE: PRT
<213> ORGANISM: Helleborus purpurascens
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(25)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(40)
<223> OTHER INFORMATION: Xaa can be any naturally occurring amino acid
<220> FEATURE:
<221> NAME/KEY: misc_feature
<222> LOCATION: (42)..(47)
<223> OTHER INFORMATION: Xaa can be any naturally occurring amino acid

<400> SEQUENCE: 15

Xaa Xaa Cys Cys Xaa Xaa Xaa Xaa Xaa Xaa Xaa Cys Xaa Xaa Xaa Cys
1               5                   10                  15

Xaa Xaa Xaa Xaa Xaa Xaa Xaa Xaa Xaa Cys Xaa Xaa Xaa Cys Xaa Cys
            20                  25                  30

Xaa Xaa Xaa Xaa Xaa Xaa Xaa Xaa Cys Xaa Xaa Xaa Xaa Xaa Xaa
        35                  40                  45
```

```
<210> SEQ ID NO 16
<211> LENGTH: 46
<212> TYPE: PRT
<213> ORGANISM: Helleborus purpurascens
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(11)
<223> OTHER INFORMATION: Xaa can be any naturally occurring amino acid
<220> FEATURE:
<221> NAME/KEY: misc_feature
<222> LOCATION: (13)..(15)
<223> OTHER INFORMATION: Xaa can be any naturally occurring amino acid
<220> FEATURE:
<221> NAME/KEY: misc_feature
<222> LOCATION: (17)..(25)
<223> OTHER INFORMATION: Xaa can be any naturally occurring amino acid
<220> FEATURE:
<221> NAME/KEY: misc_feature
<222> LOCATION: (27)..(29)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (33)..(39)
<223> OTHER INFORMATION: Xaa can be any naturally occurring amino acid
<220> FEATURE:
<221> NAME/KEY: misc_feature
<222> LOCATION: (41)..(46)
<223> OTHER INFORMATION: Xaa can be any naturally occurring amino acid

<400> SEQUENCE: 16

Xaa Xaa Cys Cys Xaa Xaa Xaa Xaa Xaa Xaa Xaa Cys Xaa Xaa Xaa Cys
 1               5                  10                  15

Xaa Xaa Xaa Xaa Xaa Xaa Xaa Xaa Xaa Cys Xaa Xaa Xaa Cys Xaa Cys
             20                  25                  30

Xaa Xaa Xaa Xaa Xaa Xaa Xaa Cys Xaa Xaa Xaa Xaa Xaa Xaa
         35                  40                  45
```

US 7,750,114 B2

PEPTIDES HAVING A HIGH CYSTEINE CONTENT

TECHNICAL FIELD

The present invention relates to peptides with a high cysteine content, to nucleic acid sequences encoding said peptides, to vectors comprising said sequences, as well as to pharmaceutical compositions containing said peptides and their use as pharmaceutics.

STATE OF THE ART

A microorganism (bacterium, virus, yeast, etc.) or a transferable agent (toxin, etc.) is referred to as pathogen, which can cause a disease or a symptom-free infection of a plant, animal or human organism. In the broader sense also insects or nematodes are referred to as pathogens, which can transfer infectious agents to organisms. Biological organisms are provided with a complex and very efficient blocking system against attacks of pathogens. It is the principal task of this blocking and immune system, respectively, to prevent the intrusion of the pathogens and to destroy the already invaded pathogens. Simple animals in this regard also possess several defense agents and protection mechanisms. The immune system of vertebrates is a very complex network of cellular and humoral mechanisms with the additional ability of being able to form specific antibodies against single pathogens and to thereby destroy them.

When the organism's own defenses are not sufficient to destroy the pathogen, additional auxiliary means have to be utilized, such as for example antibiotics, fungicides, antiviral and other agents. However a serious problem of this chemical control of pathogens is the fact, that the pathogen strains very often gain resistance to the utilized means. This adaptation can be overcome temporarily with increasing doses of active agent, but in the long term new chemical and biological means will always be required for the control of pathogens.

Peptides are compounds composed of amino acids, which are referred to as di-, tri-, oligo- or polypeptides depending on the number of the contained amino acid units. In the case of proteins polypeptides with a molar mass greater 10 kDa are concerned. In the scope of the present invention the term "peptide" is used for polypeptides with a molar mass smaller than 10 kDa. Proteins and peptides, respectively, are significantly involved in almost all of the cellular processes. Their central position in the processes of life is mirrored in that the genetic information is eventually expressed in the form of polypeptides.

On the basis of their biological tasks proteins are referred to as enzymes, transport, structure, defense, contractile, receptor proteins etc. In other biological tasks peptides and some mostly smaller proteins stand to the fore, such as the hormone effect (e.g. insulin, oxytocin), signal transmission to receptors (e.g. encephalins), control of the immune defense (cytokines) or non-specific defense (e.g. defensine). Many biologically highly effective peptides are released from bigger precursor proteins generally just at the location of action. Thus, they can display optimal effect.

The use of peptides as a pharmaceutical is very limited despite their high pharmacological effectiveness, their low toxicity and their good biocompatibility. A basic barrier consists in, that in the organism peptides are decomposed mostly very rapidly and are made ineffective thereby. It has been attempted for a long-time to prevent this rapid metabolization through the integration of hydrolysis resistant structural elements such as for example D-amino acids or by some other way. The problem is, that the therapeutical effectiveness is affected very strongly through such structural changes.

Per orally administered proteins/peptides are decomposed in the gastrointestinal tract and thus are made virtually ineffective. Hence this path of administration is very problematic for peptide pharmaceutics. Due to this reason the body-identic peptides such as insulin, erythropoietin, etc., which are used in therapy, are administered predominantly (>90%) only parenterally (through injections).

Another technical problem for the application of larger peptides is their preparation at an industrial scale, which could be solved satisfactorily only in a few cases up to now.

Contrary to the body's own peptides the parenteral application of body-alien polypeptides has to overcome a basic difficulty. The immune system of all of the higher organisms forms specific antibodies against such "non-self" peptides, which try to neutralize and to remove the alien peptide, respectively. This antigenity of alien peptides can be suppressed only artificially, e.g. by means of immunosuppressives, or by complicated constructs, whereby further side effects can be caused. As the newest example ethanercept (anti-TNF receptor protein), which is used in the therapy of rheumatoid arthritis, can be mentioned.

Body-alien polypeptides are decomposed by proteolytic enzymes in the organism. The smaller peptide segments, which are formed thereby, elicit antigen reactions, which lead to the formation of antibodies. Polypeptides, which are stable against proteolytic enzymes, should also principally exhibit a clearly smaller antigenity. Substances, which inhibit proteolytic enzymes effectively, can be used in the therapy of several pathologies. Such protease inhibitors were already utilized for the treatment of the HIV infection.

Thionins are small, extremely basic peptides of plant origin, which are characterized in an unusually high content of cysteine. The thionins are mostly composed of 45 to 48 amino acid units (Römpp Lexikon der Chemie 9. Edition, Thieme Verlag Stuttgart 1992). They contain mostly 6 or 8 cysteine groups, which form 3 or 4 intramolecular disulfide bridges (—S—S—) accordingly and thereby additionally stabilize the structure of the peptide. Due to their relatively low (about 5 kDa) molecular weight and their exceptionally stable structure it is to be expected that thionins feature more pharmacologically specific properties, which however were recognized and used only to a minor extent up to now.

In the technical literature only about 50 single thionins have been described up to now. The most known thionins are viscotoxins from mistletoe (*Viscum album*), hordothionins from barley (*Hordeum vulgaris*), purothionins from wheat (*Triticum sativum*), avenothionins from oat (*Avena-sativa*), pyrulariathionins from buffalo nut (*Pyrularia-pubera*) and crambin from *Crambus abessinicus* (D. E. A. Florack and W. J. Stiekema, Plant. Mol. Biol. 26, 25-37 (1994)).

The exact physiologic effect of the plant thionins could not be clarified clearly up to now. It was observed in the case of some thionin producing plants, that in the case of infections with bacteria or fungi these react with an increased expression of their thionins. It was assumed for this reason, that thionins could fulfill some kind of function as a defense agent. Consequently the integration of thionin genes from oat (*Avena sativa*) into other, thionin-free economic plants was carried out with the intention to breed novel types of economic plants (e.g. rice or potato) with an increased resistance against fungi and bacteria (U.S. Pat. No. 5,942,663; U.S. Pat. No. 6,187, 995).

Through the integration of the alpha-thionin gene sequences from barley into the genome of the tobacco plant e.g. a tobacco type was created with a resistance against

*Pseudomonas syringae* (M. J. Carmona, A. Molina, J. A. Lopez-Fando and F. Garcia-Olmedo, Plant J. 3, 457-462 (1993)). The inhibition of *Phytophora infestans* on potato leaf by thionins was also described (A. Molina, P. A. Groy, A. Fraile, R. Sanchez-Monge and F. Garcia-Olmedo, Plant Science 92, 672-679 (1993)).

The integration of thionin producing genes opens the way for the breeding of a large variety of novel plant types with a clearly increased resistance against pests. Thereby the use of pesticides, which intensely pollute humans and the environment, could clearly be reduced. The essential precondition for this type of use, besides the high effectiveness of the utilized thionins, is their preferably low toxicity for animals and humans. The effectiveness of a particular thionin is most efficient only against particular pests and pathogens, respectively, such that new thionin structures have to be found for the battle against further pathogens.

Thionins are very often referred to as generally toxic for animals, insects, bacteria, yeast and mammal cells (D. E. A. Florack and W. J. Stiekema, Plant. Mol. Biol. 26, 25-37 (1994)). However single thionins feature a toxicity differing very strongly from one another, which is dependent on both the structure of the thionins and the precise method of administration. Viscotoxin B for example shows a low toxicity, although its structure only differs at 4 amino acid positions from the sequence of the clearly more toxic viscotoxin A-1. The toxic effect of different thionins is explained in general by the permeabilization of the cytosolic membrane for alkali ions and the necrosis of the cells caused thereby. The mechanism of action on cellular level was investigated in some cases in detail such as e.g. the formation of membrane ion channels by Pyrularia thionins (Hughes P. et al J. Biol. Chem. (2000) 275, 823-827). However it was shown in a study carried out recently, that viscotoxins are toxic for human lymphocytes, but purothionins from wheat do not exert a toxic effect on the same lymphocytes (Büssing A. et al. Eur. J. Biochem. (1999) 262, 79-87).

Considerable amounts of thionins are present in the most corn types used for nutrition, they are also contained in numerous feeding stuffs and comestible goods. The per oral toxicity of these thionins was found to be mostly not significant for humans and animals, probably because of the decomposition of the thionins in the gastrointestinal tract and because of the thermal decomposition in the oven.

A direct human therapeutic use of a thionin as pure substance or of a standardized mixture of pure thionins has not been described in the technical literature up to now.

It is known that some preparations from mistletoe (*Viscum album*), used for a long time in adjuvant cancer therapy, contain smaller amounts of thionins which are referred to as viscotoxins. However, regarding the oncological effectiveness of these viscotoxins however there is no reliable knowledge present. Several authors even suggest explicitly, that the viscotoxins do not possess relevance for the cancer therapeutic effectiveness of the mistletoe preparations (U.S. Pat. No. 5,547,674).

The commercially available mistletoe preparations are for this reason not standardized on their viscotoxin content. Their actual viscotoxin concentration is variable, but lies in all of the cases under the limit of 1 μg/ml. From the normal dose of 2-4 ml mistletoe extract injection solution thus a patient receives 0.004 mg viscotoxin per day at maximum. With the determined toxicity of the viscotoxins of $LD_{50}$=0.1-1 mg/kg in the case of mammals, in fact no relevant cytotoxic effect can occur in the case of a mature human (70 kg body weight), which could lead to the killing of tumour cells.

In the technical literature the oncological effectiveness of the mistletoe preparations is predominantly accredited to the lectins (sugar binding proteins) contained in the extract (DE 4 221 836). These mistletoe lectins show an immunostimulating effect in low dosages (1 ng/kg), which was confirmed in vitro several times (EP-A-0 602 686). As a result several commercially available mistletoe preparations are standardized on their content of mistletoe lectins. Nonetheless the in vivo cancer therapeutic effectiveness of pure isolated mistletoe lectins could not be confirmed. Hence several authors assume a contribution from mistletoe polysaccharides or from further components of the mistletoe extracts not identified up to now (J. R. Ochocka and A. Piotrowski, Can. J. Plant Pathol. 24, 21-28 (2002)).

Latterly it was proposed to utilize the immunostimulating effect of the Pyrularia thionin observed at lower concentrations for the control of tumors (WO 02/22159). WO 02/22159 describes also the use of the thionin together with the strongly stimulating IL-2. In this context it is a concern, that a strong but non-specific immunostimulation also enhances the growth of the cancer cells, according to experience even more so than the growth of normal cells.

Thionins, which are clearly more toxic against cancer cells than against normal cells, would be very suitable for the therapy of cancer. However such thionins could not be identified up to now. It was proposed (WO 96/41608) to bind a Pyrularia thionin to particular CD5+ antibodies, which are specifically targeted against cancer cells. This complex should be then used for the selective control of cancer cells.

Cancer is not a uniform disease but a generic term for more than 200 different forms of malignant diseases. Almost every tissue can cause cancer-like degenerations, sometimes even several different types. Despite of this dissimilitude obviously all tumors are generated through the degeneration of similar basic processes.

The established therapies for cancer try to controvert the basic characteristics of the disease, namely growth, invasion and metastization. For the treatment of cancer chemotherapeutics are very important means which are utilized besides surgery and radiation. Particular malignant tumors (testicular cancer) can be treated with cytostatics successfully. Unfortunately the most frequent malignant tumors (cancer of the breast, lungs and prostate as well as colon) can not be cured by means of the chemotherapy. If the development of the tumor can not be stopped the cancer cells become more and more aggressive and start to spread themselves after a particular phase (metastasis) and to damage vitally important organs until inoperability. Thereby they lead to the death of the patients.

A basic disadvantage of the cytotoxic cancer therapeutics acting non-selectively lies in that they also kill numerous healthy cells. Hence severe side effects have to be taken into account in the case of their use. Another disadvantage of the actual chemotherapies is that the tumour cells are developing resistances against the utilized cytostatics during the treatment. This requires the constant increasing of the applied dose rate, with which an increase of the toxic side effects is simultaneously connected, or the use of a mixture of several cytostatics.

AIDS is a complex disease syndrome with chronic damaging of the T4 lymphocytes and further immune cells, which forms due to an infection with the HIV retroviruses. The common immune deficiency referred to as AIDS establishes only after the immune system has lost the struggle against the infection. In the AIDS phase the patient does not have an immune defense against different, mostly minor, infections and dies as the consequence of such diseases.

During the search of factors which participate in the regulation of the cellular and humoral immune processes in addition to polypeptides, the novel class of the carbon suboxide derivatives was recently discovered (DE 196 00 301, EP 0874 851). These natural compounds derived from inorganic carbon suboxide $C_3O_2$ feature inter alia a surprisingly specific interaction with certain immunologically important proteins such as immunoglobulins (Ig) or $F_c$ receptors. Further it was ascertained, that these carbon suboxide derivatives are capable of influencing significantly the pharmacological-toxicological properties of the peptides described herein but also of other peptides having high cysteine content.

DESCRIPTION OF THE INVENTION

Objective of the present invention is to provide peptides, which support the natural defenses of herbal, animal or human organisms against bacterial, fungal, viral or other pathogens. This objective is solved according to invention by the pharmaceutical composition according to claims 3 and 4 which comprises one or more isolated cysteine containing peptide according to claim 1. Further advantageous aspects, details and designs of the invention result from the dependent claims, the description and the drawings.

The configuration of the peptides according to invention is illustrated in the one-letter code of the amino acids as follows, namely: A: alanine, C: cysteine, D: aspartic acid, E: glutamic acid, F: phenylalanine, G: glycine, H: histidine, I: isoleucine, K: lysine, L: leucine, M: methionine, N: asparagine, P: proline, Q: glutamine, R: arginine, S: serine, T: threonine, V: valine, W: tryptophan and Y: tyrosine.

The secondary, tertiary and quaternary structure of peptides is significantly defined by the type of the side chains of the amino acids from which the respective peptide is constructed. In this context the naturally occurring amino acids can be divided into groups, where the type of the side chain represents the classification criteria. Amino acids with aliphatic side chains are glycine, alanine, valine, leucine and isoleucine. Amino acids with aliphatic side chains with hydroxyl group are serine and threonine. Amino acids with aromatic side chains are phenylalanine, tyrosine and tryptophan. Amino acids with basic side chains are lysine, arginine and histidine. Amino acids with acid side chains are aspartate and glutamate. Amino acids with amide side chains are asparagine and glutamine. Amino acids with sulphur containing side chains are cysteine and methionine. The amino acid proline has a secondary amino group and can not be divided into one of the mentioned classes. A special significance for the influencing of the three dimensional structure and hence also an influencing of the biological effectiveness can especially result through the formation of the ester derivatives of the amino acids containing hydroxyl groups. The ester formation can be conducted preferably with phosphoric acid. A suchlike derivatization can be carried out chemically-synthetically or enzymatically by means of so called phospho-kinases.

The present invention refers to cysteine containing peptides of the structure XXCCXXXXXXXCXXX-CXXXXXXQXXCXXXCXCXXXXXXXCXXXXXX (SEQ ID NO: 12), of the structure XXCCXXXXXXX-CXXXCXXXXXXXXXCXXXCXCXXXXTXXCXXXX-XX (SEQ ID NO: 13) and of the structure XXC-CXXXXXXXCXXXCXXXXXXXXXCXXXCXCXXX-XXXXXCXXXXXX (SEQ ID NO: 14), wherein X represents a replacement character. All of the X can be chosen independently from one another and mean any of the above mentioned naturally occurring amino acids.

As naturally occurring amino acids are included in addition to the established L-amino acids also D-amino acids as well as amino acid derivatives such as for example 4-hydroxyproline, N,N,N-trimethyllysine, 3-methylhistidine, 5-hydroxylysine, O-phosphoserine, γ-carboxyglutamate, ε-N-acetyllysine, ω-N-methylarginine, citrulline or ornithine.

The disulphide bridges are formed preferably between the cysteines shown in the following, such that the following preferred structures are resulting:

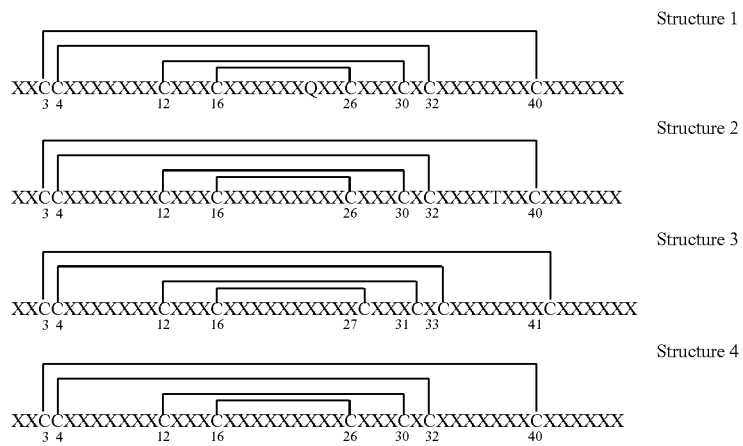

Especially preferred embodiments of the present invention refer to cysteine containing peptides of the mentioned general structures, whereas further amino acids are defined at certain positions of the peptide. Preferred are peptides, wherein at position 1 the amino acid K and/or at position 2 the amino acid S and/or at position 5 the amino acid R and/or at position 6 the amino acid N and/or at position 7 the amino acid T and/or at position 8 the amino acid L and/or at position 10 the amino acid R and/or at position 11 the amino acid N and/or at position 13 the amino acid Y and/or at position 17 the amino acid R and/or at position 20 the amino acid G is located.

Further preferred are the following peptides of the structure 1 and of the structure XXCCXXXXXXXCXXX-CXXXXXXQXXCXXXCXCXXXXXXXCXXXXXX (SEQ ID NO: 12), respectively, wherein at position 15 the amino acid G and/or at position 19 the amino acid T and/or at position 27 the amino acid Q and/or at position 28 the amino acid R and/or at position 31 the amino acid D and/or at position 33 the amino acid I and/or at position 34 the amino acid H and/or at position 35 the amino acid V and/or at position 36 the amino acid T and/or at position 37 the amino acid T and/or at position 38 the amino acid T and/or at position 43 the amino acid S and/or at position 44 the amino acid H and/or at position 46 the amino acid S is located.

Further preferred are the following peptides of the structure 2 and of the structure XXCCXXXXXXXCXXX-CXXXXXXXXXCXXXCXCXXXXTXXCXXXXXX (SEQ ID NO: 13), respectively, wherein at position 15 the amino acid G and/or at position 19 the amino acid T and/or at position 23 the amino acid Q and/or at position 27 the amino acid Q and/or at position 28 the amino acid R and/or at position 31 the amino acid D and/or at position 33 the amino acid I and/or at position 34 the amino acid H and/or at position 35 the amino acid V and/or at position 36 the amino acid T and/or at position 38 the amino acid T and/or at position 43 the amino acid S and/or at position 44 the amino acid H and/or at position 46 the amino acid S is located.

Further preferred are the following peptides of the structure 3 and of the structure XXCCXXXXXXXCXXX-CXXXXXXXXXCXXXCXCXXXXXXXXCXXXXXX (SEQ ID NO: 15), respectively, wherein the following amino acid combinations are residing:

| Position | AS | | Position | AS | | Position | AS | |
|---|---|---|---|---|---|---|---|---|
| 15 | G | and | 19 | T | or | 23 | Q | or |
|  |  |  | 28 | G | or | 29 | R | or |
|  |  |  | 32 | D | or | 34 | I | or |
|  |  |  | 35 | H | or | 36 | V | or |
|  |  |  | 37 | T | or | 38 | T | or |
|  |  |  | 39 | T | or | 44 | S | or |
|  |  |  | 45 | H | or | 47 | S |  |
| 19 | T | and | 15 | G | or | 23 | Q | or |
|  |  |  | 28 | G | or | 29 | R | or |
|  |  |  | 32 | D | or | 34 | I | or |
|  |  |  | 35 | H | or | 36 | V | or |
|  |  |  | 37 | T | or | 38 | T | or |
|  |  |  | 39 | T | or | 44 | S | or |
|  |  |  | 45 | H | or | 47 | S |  |
| 20 | T | and | 15 | G | or | 23 | Q | or |
|  |  |  | 28 | G | or | 29 | R | or |
|  |  |  | 32 | D | or | 34 | I | or |
|  |  |  | 35 | H | or | 36 | V | or |
|  |  |  | 37 | T | or | 38 | T | or |
|  |  |  | 39 | T | or | 44 | S | or |
|  |  |  | 45 | H | or | 47 | S |  |
| 23 | Q | and | 15 | G | or | 19 | T | or |
|  |  |  | 28 | G | or | 29 | R | or |
|  |  |  | 32 | D | or | 34 | I | or |
|  |  |  | 35 | H | or | 36 | V | or |
|  |  |  | 37 | T | or | 38 | T | or |
|  |  |  | 39 | T | or | 44 | S | or |
|  |  |  | 45 | H | or | 47 | S |  |
| 24 | Q | and | 15 | G | or | 19 | T | or |
|  |  |  | 28 | G | or | 29 | R | or |
|  |  |  | 32 | D | or | 34 | I | or |
|  |  |  | 35 | H | or | 36 | V | or |
|  |  |  | 37 | T | or | 38 | T | or |
|  |  |  | 39 | T | or | 44 | S | or |
|  |  |  | 45 | H | or | 47 | S |  |
| 28 | Q | and | 15 | G | or | 19 | T | or |
|  |  |  | 23 | Q | or | 29 | R | or |
|  |  |  | 32 | D | or | 34 | I | or |
|  |  |  | 35 | H | or | 36 | V | or |
|  |  |  | 37 | T | or | 38 | T | or |
|  |  |  | 39 | T | or | 44 | S | or |
|  |  |  | 45 | H | or | 47 | S |  |
| 29 | R | and | 15 | G | or | 19 | T | or |
|  |  |  | 23 | Q | or | 29 | R | or |
|  |  |  | 32 | D | or | 34 | I | or |
|  |  |  | 35 | H | or | 36 | V | or |
|  |  |  | 37 | T | or | 38 | T | or |
|  |  |  | 39 | T | or | 44 | S | or |
|  |  |  | 45 | H | or | 47 | S |  |
| 32 | D | and | 15 | G | or | 19 | T | or |
|  |  |  | 23 | Q | or | 28 | Q | or |
|  |  |  | 29 | R | or | 34 | I | or |
|  |  |  | 35 | H | or | 36 | V | or |
|  |  |  | 37 | T | or | 38 | T | or |
|  |  |  | 39 | T | or | 44 | S | or |
|  |  |  | 45 | H | or | 47 | S |  |
| 34 | I | and | 15 | G | or | 19 | T | or |
|  |  |  | 23 | Q | or | 28 | Q | or |
|  |  |  | 29 | R | or | 32 | D | or |
|  |  |  | 35 | H | or | 36 | V | or |
|  |  |  | 37 | T | or | 38 | T | or |
|  |  |  | 39 | T | or | 44 | S | or |
|  |  |  | 45 | H | or | 47 | S |  |
| 35 | H | and | 15 | G | or | 19 | T | or |
|  |  |  | 23 | Q | or | 28 | Q | or |
|  |  |  | 29 | R | or | 32 | D | or |
|  |  |  | 34 | I | or | 36 | V | or |
|  |  |  | 37 | T | or | 38 | T | or |
|  |  |  | 39 | T | or | 44 | S | or |
|  |  |  | 45 | H | or | 47 | S |  |
| 36 | V | and | 15 | G | or | 19 | T | or |
|  |  |  | 23 | Q | or | 28 | Q | or |
|  |  |  | 29 | R | or | 32 | D | or |
|  |  |  | 34 | I | or | 35 | H | or |
|  |  |  | 37 | T | or | 38 | T | or |
|  |  |  | 39 | T | or | 44 | S | or |
|  |  |  | 45 | H | or | 47 | S |  |
| 37 | T | and | 15 | G | or | 19 | T | or |
|  |  |  | 23 | Q | or | 28 | Q | or |
|  |  |  | 29 | R | or | 32 | D | or |
|  |  |  | 34 | I | or | 35 | H | or |
|  |  |  | 36 | V | or | 38 | T | or |
|  |  |  | 39 | T | or | 44 | S | or |
|  |  |  | 45 | H | or | 47 | S |  |
| 38 | T | and | 15 | G | or | 19 | T | or |
|  |  |  | 23 | Q | or | 28 | Q | or |
|  |  |  | 29 | R | or | 32 | D | or |
|  |  |  | 34 | I | or | 35 | H | or |
|  |  |  | 36 | V | or | 37 | T | or |
|  |  |  | 39 | T | or | 44 | S | or |
|  |  |  | 45 | H | or | 47 | S |  |
| 39 | T | and | 15 | G | or | 19 | T | or |
|  |  |  | 23 | Q | or | 28 | Q | or |
|  |  |  | 29 | R | or | 32 | D | or |
|  |  |  | 34 | I | or | 35 | H | or |
|  |  |  | 36 | V | or | 37 | T | or |
|  |  |  | 38 | T | or | 44 | S | or |
|  |  |  | 45 | H | or | 47 | S |  |
| 44 | S | and | 15 | G | or | 19 | T | or |
|  |  |  | 23 | Q | or | 28 | Q | or |
|  |  |  | 29 | R | or | 32 | D | or |
|  |  |  | 34 | I | or | 35 | H | or |
|  |  |  | 36 | V | or | 37 | T | or |
|  |  |  | 38 | T | or | 39 | T | or |
|  |  |  | 45 | H | or | 47 | S |  |
| 45 | H | and | 15 | G | or | 19 | T | or |
|  |  |  | 23 | Q | or | 28 | Q | or |
|  |  |  | 29 | R | or | 32 | D | or |
|  |  |  | 34 | I | or | 35 | H | or |
|  |  |  | 36 | V | or | 37 | T | or |
|  |  |  | 38 | T | or | 39 | T | or |
|  |  |  | 44 | S | or | 47 | S |  |
| 47 | S | and | 15 | G | or | 19 | T | or |
|  |  |  | 23 | Q | or | 28 | Q | or |
|  |  |  | 29 | R | or | 32 | D | or |
|  |  |  | 34 | I | or | 35 | H | or |
|  |  |  | 36 | V | or | 37 | T | or |
|  |  |  | 38 | T | or | 39 | T | or |
|  |  |  | 44 | S | or | 45 | H |  |

Further preferred are the following peptides of the structure 4 and of the structure XXCCXXXXXXXCXXX-CXXXXXXXXXCXXXCXCXXXXXXXCXXXXXX (SEQ ID NO: 16), respectively, wherein the following amino acid combinations are residing:

| Position | AS |     | Position | AS |     | Position | AS |     |
|----------|----|----|----------|----|----|----------|----|----|
| 15 | G | and | 19 | T | or | 27 | Q | or |
|    |   |     | 28 | R | or | 31 | D | or |
|    |   |     | 33 | I | or | 34 | H | or |
|    |   |     | 35 | V | or | 36 | T | or |
|    |   |     | 37 | T | or | 38 | T | or |
|    |   |     | 43 | S | or | 44 | H | or |
|    |   |     | 46 | S |    |    |   |    |
| 19 | T | and | 15 | G | or | 27 | Q | or |
|    |   |     | 28 | R | or | 31 | D | or |
|    |   |     | 33 | I | or | 34 | H | or |
|    |   |     | 35 | V | or | 36 | T | or |
|    |   |     | 37 | T | or | 38 | T | or |
|    |   |     | 43 | S | or | 44 | H | or |
|    |   |     | 46 | S |    |    |   |    |
| 27 | Q | and | 15 | G | or | 19 | T | or |
|    |   |     | 28 | R | or | 31 | D | or |
|    |   |     | 33 | I | or | 34 | H | or |
|    |   |     | 35 | V | or | 36 | T | or |
|    |   |     | 37 | T | or | 38 | T | or |
|    |   |     | 43 | S | or | 44 | H | or |
|    |   |     | 46 | S |    |    |   |    |
| 28 | R | and | 15 | G | or | 19 | T | or |
|    |   |     | 27 | Q | or | 31 | D | or |
|    |   |     | 33 | I | or | 34 | H | or |
|    |   |     | 35 | V | or | 36 | T | or |
|    |   |     | 37 | T | or | 38 | T | or |
|    |   |     | 43 | S | or | 44 | H | or |
|    |   |     | 46 | S |    |    |   |    |
| 31 | D | and | 15 | G | or | 19 | T | or |
|    |   |     | 27 | Q | or | 28 | R | or |
|    |   |     | 33 | I | or | 34 | H | or |
|    |   |     | 35 | V | or | 36 | T | or |
|    |   |     | 37 | T | or | 38 | T | or |
|    |   |     | 43 | S | or | 44 | H | or |
|    |   |     | 46 | S |    |    |   |    |
| 33 | I | and | 15 | G | or | 19 | T | or |
|    |   |     | 27 | Q | or | 28 | R | or |
|    |   |     | 31 | D | or | 34 | H | or |
|    |   |     | 35 | V | or | 36 | T | or |
|    |   |     | 37 | T | or | 38 | T | or |
|    |   |     | 43 | S | or | 44 | H | or |
|    |   |     | 46 | S |    |    |   |    |
| 34 | H | and | 15 | G | or | 19 | T | or |
|    |   |     | 27 | Q | or | 28 | R | or |
|    |   |     | 31 | D | or | 33 | I | or |
|    |   |     | 35 | V | or | 36 | T | or |
|    |   |     | 37 | T | or | 38 | T | or |
|    |   |     | 43 | S | or | 44 | H | or |
|    |   |     | 46 | S |    |    |   |    |
| 35 | V | and | 15 | G | or | 19 | T | or |
|    |   |     | 27 | Q | or | 28 | R | or |
|    |   |     | 31 | D | or | 33 | I | or |
|    |   |     | 34 | H | or | 36 | T | or |
|    |   |     | 37 | T | or | 38 | T | or |
|    |   |     | 43 | S | or | 44 | H | or |
|    |   |     | 46 | S |    |    |   |    |
| 36 | T | and | 15 | G | or | 19 | T | or |
|    |   |     | 27 | Q | or | 28 | R | or |
|    |   |     | 31 | D | or | 33 | I | or |
|    |   |     | 34 | H | or | 35 | V | or |
|    |   |     | 37 | T | or | 38 | T | or |
|    |   |     | 43 | S | or | 44 | H | or |
|    |   |     | 46 | S |    |    |   |    |
| 38 | T | and | 15 | G | or | 19 | T | or |
|    |   |     | 27 | Q | or | 28 | R | or |
|    |   |     | 31 | D | or | 33 | I | or |
|    |   |     | 34 | H | or | 35 | V | or |
|    |   |     | 36 | T | or | 37 | T | or |
|    |   |     | 43 | S | or | 44 | H | or |
|    |   |     | 46 | S |    |    |   |    |
| 43 | S | and | 15 | G | or | 19 | T | or |
|    |   |     | 27 | Q | or | 28 | R | or |
|    |   |     | 31 | D | or | 33 | I | or |
|    |   |     | 34 | H | or | 35 | V | or |
|    |   |     | 36 | T | or | 37 | T | or |
|    |   |     | 38 | T | or | 44 | H | or |
|    |   |     | 46 | S |    |    |   |    |
| 44 | H | and | 15 | G | or | 19 | T | or |
|    |   |     | 27 | Q | or | 28 | R | or |
|    |   |     | 31 | D | or | 33 | I | or |
|    |   |     | 34 | H | or | 35 | V | or |
|    |   |     | 36 | T | or | 37 | T | or |
|    |   |     | 38 | T | or | 43 | S | or |
|    |   |     | 46 | S |    |    |   |    |
| 46 | S | and | 15 | G | or | 19 | T | or |
|    |   |     | 27 | Q | or | 28 | R | or |
|    |   |     | 31 | D | or | 33 | I | or |
|    |   |     | 34 | H | or | 35 | V | or |
|    |   |     | 36 | T | or | 37 | T | or |
|    |   |     | 38 | T | or | 43 | S | or |
|    |   |     | 44 | H |    |    |   |    |

The abbreviation AS represents amino acid.

Very especially preferred are cysteine containing peptides of the structure KSCCRNTLGRNCYNGCRFTGGSQPTCGRLCDCIHVTTTTCPSSHPS (SEQ ID NO: 1), (hellethionin-A), KSCCRNTLGRNCYNACRFTGGSQPTCGRLCDCIHVTTTTCPSSHPS (SEQ ID NO: 2), (hellethionin-B1), KSCCRNTLARNCYNACRFTGGSQPTCGRLCDCIHVTTTTCPSSH PS (SEQ ID NO: 3), (hellethionin-B2), KSCCRNTLGRNCYNACRLPGTPQPTCATLCDCIHVTTPTCPSSHPR (SEQ ID NO: 4), (hellethionin-B3), KSCCRNTLARNCYNACRFTGTSQPYCARLCDCIHVTTPTCPSSHPR (SEQ ID NO: 5), (hellethionin-B4), KSCCRNTLARNCYNACRFTGGSQPTCATLCDCIHVTTPTCPSSHPR (SEQ ID NO: 6), (hellethionin-B5), KSCCRNTLARNCYNVCRFGGGSQAYCARFCDCIHVTTSTCPSSH PS (SEQ ID NO: 7), (hellethionin-B6), KSCCRNTLGRNCYNACRLTGTSQATCATLCDCIHVTATTCRPPYPS (SEQ ID NO: 8), (hellethionin-C), KSCCRNTLARNCYNACRFTGGSQPTCGILCDCIHVTTTTCPSSH PS (SEQ ID NO: 9), (hellethionin-D), KSCCRNTLGRNCYMCRLTGLFSQEQCARLCDCITVTTPTPCPRTH PS (SEQ ID NO: 10), (hellethionin-E1) and KSCCRNTLGRNCYMCRLTGTFSQEQCARLCDCITVTTPTPCPRTHPS (SEQ ID NO: 11), (hellethionin-E2).

Especially preferred are further derivatives of the aforementioned hellethionins, i.e. derivatives of hellethionin-A, hellethionin-B1, hellethionin-B2, hellethionin-B3, hellethionin-B4, hellethionin-B5, hellethionin-B6, hellethionin-C, hellethionin-D and hellethionin-E1, wherein the following amino acids (initial AS) have been replaced by the amino acids (substitution AS) listed on the side:

| Initial AS | Substitution AS |
|------------|-----------------|
| Ala | Ser |
| Arg | Lys |
| Asn | Gln or His |
| Asp | Glu |
| Cys | Ser |
| Gln | Asn |
| Glu | Asp |
| Gly | Pro |
| His | Asn or Gln |

-continued

| Initial AS | Substitution AS |
|---|---|
| Ile | Leu or Val |
| Leu | Ile or Val |
| Lys | Arg or Gln or Glu |
| Met | Leu or Ile |
| Phe | Met or Leu or Tyr |
| Ser | Thr |
| Thr | Ser |
| Trp | Tyr |
| Tyr | Trp or Phe |
| Val | Ile or Leu |

Further also the use of peptidomimetics is possible. Herein chemical substances are concerned, which imitate one of the afore-mentioned peptides.

The present invention also comprises ester derivatives, amide derivatives, salt derivatives, cyclic derivatives and derivatives with a modified backbone of the mentioned peptides.

Amino acids with carboxylate groups can be transferred for example into a salt, or into an ester, preferred into a $C_1$-$C_{16}$ ester or an amide, optionally with one or two alkyl moieties, preferred with $C_1$-$C_{16}$ alkyl moieties. Hydroxyl groups of for example tyrosine or serine can be transferred into an ester or ether. Further also the formation of acetals, ketals or carbonates is possible. Such moieties preferably consist of 1 to 16 carbon atoms. Further all of the other known OH protecting groups can be utilized. The alkyl moieties used in the protecting groups can bear further substituents for example halogens, amino groups, hydroxyl groups, carbonyl groups, thiol groups, aryl groups, alkyl branchings, carboxyl groups, nitro groups, amide groups and/or ester groups.

Very especially preferred in the scope of the present invention are the cysteine containing peptide compounds hellethionin-A, hellethionin-B1, hellethionin-B2, hellethionin-B3, hellethionin-B4, hellethionin-B5, hellethionin-B6, hellethionin-C, hellethionin-D, hellethionin-E1 and hellethionin-E2 as well as derivatives of these cysteine containing peptide compounds with amino acid variations at up to 15 positions of the cysteine containing peptide compound respectively at up to 15 positions of the derivatives of these cysteine containing peptide compounds, whereas the amino acid cysteine is not subject to variation regarding position and type. It is especially preferred, if the amino acid variations occur at up to 13 positions, at up to 11 positions, at up to 9 positions, at up to 7 positions, at up to 5 positions, at up to 4 positions, at up to 3 positions, at up to 2 positions and only at one position, respectively, of the peptide compounds and of the derivatives of the peptide compounds, respectively.

It is especially preferred, if the cysteine containing peptide compounds, hellethionin-A, hellethionin-B1, hellethionin-B2, hellethionin-B3, hellethionin-B4, hellethionin-B5, hellethionin-B6, hellethionin-C, hellethionin-D, hellethionin-E1 and hellethionin-E2 as well as derivatives of these cysteine containing peptide compounds feature one of the above-mentioned amounts of amino acid variations and if simultaneously at position 1 the amino acid K and/or at position 2 the amino acid S and/or at position 5 the amino acid R and/or at position 6 the amino acid N and/or at position 7 the amino acid T and/or at position 8 the amino acid L and/or at position 10 the amino acid R and/or at position 11 the amino acid N and/or at position 13 the amino acid Y and/or at position 17 the amino acid R and/or at position 20 the amino acid G is located.

Especially preferred embodiments of the present invention refer to cysteine containing peptides of the mentioned general structures, wherein amino acids are located at particular positions of the peptide, which are selected from a particular group of amino acids defined above. Preferred are peptides, wherein at position 1 an amino acid with basic side chain and/or at position 2 an amino acid with aliphatic side chain with hydroxyl group and/or at position 5 an amino acid with basic side chain and/or at position 6 an amino acid with amide side chain and/or at position 7 an amino acid with aliphatic side chain with hydroxyl group and/or at position 8 an amino acid with aliphatic side chain and/or at position 10 an amino acid with basic side chain and/or at position 11 an amino acid with amide side chain and/or at position 13 an amino acid with aromatic side chain and/or at position 17 an amino acid with basic side chain and/or at position 20 an amino acid with aliphatic side chain is located.

Of course the present invention comprises also peptides of the mentioned general structures, which are bearing functional modifications at one or at both of their ends. Especially comprised are also peptides having longer chains, i.e. peptides, the amino acid chain of which exceeds the mentioned general structures. Thus the peptides according to the invention represent in these cases only a section of a greater peptide. The functionality of the peptides according to the invention, and so their effectivity, may not be influenced significantly by these functional modifications.

From the structures 1-4 according to the invention as well as the formulas XXCCXXXXXXXCXXXCXXXXXX-QXXCXXXCXCXXXXXXXCXXXXX (SEQ ID NO: 12), XXCCXXXXXXXCXXXCXXXXXXXX-CXXXXCXCXXXXTXXCXXXXXX (SEQ ID NO: 13), and XXCCXXXXXXXCXXXCXXXXXXXXX-CXXXXCXCXXXXXXXCXXXXXX (SEQ ID NO: 14), according to the invention also peptides are comprised, which are bearing before the X at position 1 and/or after the X at position 46 and 47, respectively, arbitrary end groups or featuring still another oligopeptide chain with up to 50 amino acids, preferred with up to 30 amino acids, more preferred with up to 15 amino acids and especially preferred with up to 7 amino acids.

In addition the present invention refers to the nucleic acid sequences, which are encoding for the mentioned cysteine containing peptides, and also to the corresponding RNA sequences and the corresponding DNA sequences as well as the corresponding anti-sense DNA and the corresponding anti-sense RNA. The present invention comprises also DNA vectors and DNA constructs, which contain a cDNA or DNA corresponding to a peptide according to the invention as well as a suitable promoter and a suitable enhancer if necessary.

In addition also monoclonal antibodies are comprised, which are targeted against an epitope of the mentioned cysteine containing peptides.

The peptides having a high cysteine content according to the invention are composed of 46 and 48 amino acids, respectively. The count of the positions is carried out starting from the free $NH_2$-end of the amino acid chain.

From the above-mentioned hellethionins the peptides referred to with hellethionin-A (HT-A), hellethionin-C (HT-C) and with hellethionin-D (HT-D) were isolated individually by the methods described in the following. In the case of hellethionin-B and hellethionin-E a mixture of several isoforms is present, whereas the amino acid sequence of six isoforms (HT-B1, HT-B2, HT-B3, HT-B4, HT-B5, HT-B6) and of two isoforms (HT-E1 and HT-E2), respectively, was determined. The peptides according to the invention can be used as pure substances, as a mixture of isoforms or as a mixture of isoforms together with one or more other hellethionins, preferably as a mixture of several hellethionins.

The amino acid sequence of the isolated or the synthetically produced peptides according to the invention was determined by successive degradation of the peptide chain according to the Edman method and subsequent HPLC identification of the PTH (phenylthiohydantoin) derivatives. The enzymatic fragmentation of the peptides usual in the case of this method could not be carried out directly due to their increased enzymatic stability. For this reason initially a reduction and opening, respectively, of the disulphide bridges carried out by means of vinylpyridine was required.

Another confirmation of the amino acid composition of the peptides according to the invention was carried out by the determination of their molar masses. For this purpose mass spectrometry with ESI (electro-spray-ionization) and the MALDI (matrix-assisted-laser-desorption-ionization) technique was utilized.

The three-dimensional structure of the peptide HT-D determined by NMR spectroscopy is illustrated in FIG. 1. The total structure is similar to the shape of a capital Greek gamma ($\Gamma$). The long arm in this structure analogy is formed through the two helices running contrarily, whereas the short arm consists of the short beta-sheet. The both helices are connected through a loop between the amino acids in the positions 17 and 24.

A special contribution to the stability of the peptides according to the invention is guaranteed through the total of four disulphide bridges between the cysteine units in the positions 3-40 (or respectively 42), 4-32, 12-30 (or respectively 31) and 16-26 (or respectively 27). The extraordinary stability obtained thereby contrary to proteolytic and other enzymes is a specific property with important meaning for the use of the peptides described herein.

The preferred peptides in the scope of the present invention are characterized in an astonishing high conservation of their amino acid sequences. This conservation pertains to up to 36 positions, thus about ¾ of the total chain. The variations in the composition of the polypeptide chain are mostly limited to 15 or even less positions.

Especially constant is the position of the cysteine moieties, which are located in the peptides according to the invention at the positions 3, 4, 12, 16, 26 or respectively 27, 30 or respectively 31, 32 and 40 or respectively 42. In the sequences referred to with HT-E1 and HT-E2 the last three cysteine units are displaced each by one (27 instead of 26) (31 instead of 30) or by two positions (42 instead of 40). The cysteine units are connected through disulphide bridges in pairs. From the numerous possible combinations of cysteine units in the peptides according to invention the connections 3→40 (or respectively 42), 4→32, 12→30 (or respectively 31) and 16→26 (or respectively 27) are preferably formed, thereby defining a particular secondary structure of the peptides according to the invention.

The use of the peptides according to the invention provides several advantages in comparison to the thionins with 3 disulphide bridges known up to now. Firstly due to the presence of the additional cysteine bridge the peptides according to invention possess an improved stability in comparison to proteolytic enzymes and show accordingly a lower immunogenity than for example the already mentioned viscotoxins. Another advantage of the peptides according to the invention lies in their surprisingly good solubility in water and in the better bioavailability achieved thereby. This advantage becomes especially clear in the comparison with the thionins with 4 disulphide bridges known up to now. The previously described thionin peptides with 4 disulphide bridges such as for example purothionins, avenothionins or hordothionins are strongly basic and very lipophilic and therefore only poorly soluble in water. They are extracted from the corresponding grain seeds by means of apolar solvents such as petrol ether. Hence aqueous solutions of these peptides are difficult to produced and are difficult to use.

Isolation and Preparation of the Peptides According to Invention

The present invention comprises also methods for the extraction of the cysteine containing peptides according to the invention. Such a method according to invention is represented by the extraction of *Helleborus* plant species. Especially preferred in this case is defatting of the plant material using non-polar solvents or mixtures of non-polar solvent, particularly using tert.-butylmethylether, carried out as the first step of the method. The isolation of the peptides having a high cysteine content according to the invention or of mixtures of the peptides according to the invention is carried out from plants of the family Ranunculaceae (buttercup family) and preferably from plants of the genus *Helleborus* (Christmas rose). Air dried plant material, preferably the subterrestrial parts of the plant (roots and rootstock) are used for the isolation. Initially the preferred defatting of the plant material is carried out with a non-polar solvent, preferably TBM (ter.-butylmethylether). The defatted and air dried roots are subsequently extracted with mixtures of organic alcohol/acid, preferably methanol/formic acid, or with solvent mixtures containing water, preferably water/ethanol, respectively with diluted acids, preferably acetic acid 0.1-12%.

The filtered extraction solution is reduced under vacuum up to ⅒ of the initial volume and then treated with an adsorption material, preferably active carbon. The filtrate is reduced under vacuum and the dry residue is resolved in a minimal amount of water. The pH value of the aqueous solution is adjusted in the acid region, preferably pH 0.1-3.0, by adding diluted hydrochloric acid. The aqueous solution is merged with a multiple, preferably tenfold, volume of a cooled organic solvent or solvent mixture, preferably ethanol/acetone 1:3. The light-yellow precipitate that is formed is filtered off, vacuum dried and used for the further purification procedure.

An alternative method for the extraction of the peptides according to the invention is carried out by their selective coupling to ion exchanger resins, preferably to slightly acidic ion exchangers. The peptides coupled to the resin are released by means of a treatment with strongly ionic solutions, preferably HCl or NaCl.

The isolation of the peptides according to the invention can also be carried out by selective coupling to special solid phases, preferred to solid phases, which enable an especially selective isolation through antigen-antibody or similar highly specific interactions.

Another method for the extraction of the peptides according to the invention is carried out by the separation of their native mixtures by means of high pressure liquid chromatography (HPLC) on a preparative scale. Mixtures of acetonitrile/water with linear gradient are used as eluents. A pH value between 1 and 1.5 is adjusted by adding a strong acid, preferably trifluoroacetic acid.

In addition the present invention relates also to methods for synthetic generation of the cysteine containing peptides according to the invention and to functional derivatives of these peptides by peptide synthesis. The synthetic generation of the peptides according to the invention is carried out through stepwise coupling of the single amino acid building blocks. Therefore automatic methods of peptide synthesis are utilized, wherein methods of solid phase and methods of liquid phase are preferred. The methods are described in detail in M. Bodanszky, Principles of Peptide Synthesis (B. M. Trost Edit.) Springer Verlag 1994.

In addition the present invention comprises the generation of the cysteine containing peptides according to the invention by methods of gene technology. Preferred is gene technological generation through the integration of genes of the peptides according to the invention into the genetic material of a plant, preferred grain types having a high protein output. An especially preferred embodiment in this context is the replacement of the thionin genes of a thionin producing grain with the thionin genes of species of the plant *Helleborus*.

The generation of the peptides according to the invention is also possible through the transgenic expression of the cDNA sequences. The identified DNA segments (as cDNA clones, as genome DNA clones or through DNA segments prepared by oligonucleotide synthesis) can be expressed in a biological system. Preferred biological systems for the expression of the cysteine containing peptides according to the invention are cultures of certain easily available microorganisms such as *Escherichia coli, Pseudomonas* or yeast.

Cell cultures of plants, into which the gene sequences encoding for the peptides according to invention are integrated, also provide good results for the generation of the peptides according to the invention. Known methods are used for the transformation of the utilised plant cells. Preferably used are Ti-plasmids of *Agrobacterium*, electroporation or micro injection. The genetically altered plant cells can be also regenerated as plants, in which the gene sequences encoding for the peptides according to invention remain stably integrated in the genome.

Special chemical modifications of the peptides can be carried out, by which an increase of the bioavailability is achieved, for the use of the peptides according to the invention in the pharmaceutical field. Hence the invention also relates to the chemical modification of the peptides according to the invention through their transformation into a macrocyclic compound, preferably by closing an additional bond between the two amino acids at the beginning and at the end or in the vicinity of both ends of the peptide chain. The synthesized macrocyclic peptide features advantageous physiological properties, especially an increased stability against proteolytic and other enzymes. For the preparation of the cyclic compounds established reagents are used such as carbodiimides, especially 1-ethyl-3-(3-dimethylaminopropyl)-carbodiimid (EDAC).

In the scope of the present invention the hellethionins can be also modified through the targeted replacement of one or more amino acid units with a natural or synthetic amino acid, preferably with an aromatic amino acid such as tyrosine. Such a modification of the amino acid sequence can be carried out by targeted mutations of the gene segment expressing a DNA sequence of the peptide according to the invention. Thereby preferably used is the SPI (selective pressure incorporation) method (C. Minks et al. in Tetrahedron, 56 (2000) 9431-9442).

A derivative, which can be generated through minor chemical conversion of one or more amino acid building blocks of the hellethionins, is also a part of the present invention. Such a derivatization leads to a targeted change of the therapeutical properties of the peptides. Preferred is the conversion of the amino acids containing hydroxyl groups such as threonine or tyrosine into ester derivatives or halogen derivatives. The conversion of the amino acids containing free COOH-moieties into ester derivatives or amide derivatives is also a part of the present invention. The alkylation, preferably methylation, of the free amino groups or of other functional groups leads to a better bioavailability and is also a part of the present invention.

Use of the Peptides

The cysteine containing peptides according to the invention, mixtures of these cysteine containing peptides and functional derivatives of these peptides can be used in the treatment of diseases, especially in the treatment of diseases caused by pathogens.

In addition the cysteine containing peptides according to the invention, mixtures of these cysteine containing peptides and functional derivatives of these peptides can be used in the treatment of diseases caused by bacteria, fungi or viruses.

The cysteine containing peptides according to the invention, mixtures of these cysteine containing peptides and functional derivatives of these peptides can be especially used in the treatment of diseases of humans and animals, especially in the case of large animals, preferably horses.

It has especial advantages to use the cysteine containing peptides according to the invention, mixtures of these cysteine containing peptides and functional derivatives of these peptides in the treatment of diseases, which are caused by defective bioregulation of the immune system or are accompanied by a defective bioregulation of the immune system.

In addition the cysteine containing peptides according to the invention, mixtures of these cysteine containing peptides and functional derivatives of these peptides can be used especially successfully in the treatment of autoimmune diseases, in the treatment of cancer and in the treatment of AIDS.

In addition the present invention comprises pharmaceutical compositions, which contain one or more cysteine containing peptides according to the invention and/or functional derivatives of these peptides. Especially preferred are pharmaceutical compositions, which comprise in addition at least one carbon suboxide derivative.

In the scope of the present invention under the term "carbon suboxide derivatives" natural substances are understood, which are derived from inorganic carbon suboxide $C_3O_2$, as they are described in DE 196 00 301, EP 0 874 851 B1 and Kerek et al., Biochim. Biophys. Acta 1567, 213-220 (2002). In this respect the disclosure of DE 196 00 301 and EP 0 874 851 B1 is incorporated into the present invention by reference. Hence, if in the scope of the present application a "carbon suboxide derivative" is mentioned, this term comprises all of the chemical compounds described in DE 196 00 301. The preparation and characterization of the carbon suboxide derivatives is also described in DE 196 00 301 and EP 0 874 851 B1.

Thus the present invention especially relates also to combined preparations of at least one of the compounds according to the invention and of at least one carbon suboxide derivative as described previously as well as in DE 196 00 301, EP 0 874 851 B1 and Kerek et al., Biochim. Biophys. Acta 1567, 213-220 (2002).

The present invention also comprises the cysteine containing peptides according to the invention, the mixtures of these cysteine containing peptides, the functional derivatives of these peptides and/or the pharmaceutically acceptable salts of these cysteine containing peptides for the preparation of a pharmaceutical composition for the treatment of diseases, especially for the treatment of diseases caused by pathogens.

In this context the preparation of a pharmaceutical composition for the prophylaxis and/or treatment of cancer provides special advantages, for example in the case of choroidal melanoma, acute leukaemia, acoustic neurinoma, ampullary carcinoma, anal carcinoma, astrocytoma, basal cell carcinoma, pancreatic cancer, bladder cancer, bronchial carcinoma, breast cancer, Burkitt's lymphoma, corpus cancer, CUP-syndrome, colorectal cancer, small intestine cancer, small intestinal tumors, ovarian cancer, endometrial carcinoma, ependymoma, epithelial cancer types, Ewing's tumors, gastrointestinal tumors, gallbladder cancer, uterine cancer, cervical cancer, glioblastomas, gynecologic tumors, throat, nose and ear tumors, hematologic neoplasias, hairy cell leukemia, urethral cancer, skin cancer, brain tumors (gliomas), brain metastases, testicle cancer, lymph node cancer (Hodgkin's/Non-Hodgkin's), hypophysis tumor, carcinoids, Kaposi's sarcoma, laryngeal cancer, germ cell tumor, bone cancer, colorectal carcinoma, head and neck tumors, colon carcinoma, craniopharyngiomas, oral cancer (cancer in the mouth area and on lips), liver cancer, liver metastases, leukemia, eyelid tumor, lung cancer, lymphomas, stomach cancer, malignant melanoma, breast carcinoma, rectal cancer, medulloblastomas, melanoma, meningiomas, Hodgkin's disease, mycosis fungoides, nasal cancer, neurinoma, kidney cancer, non-Hodgkin's lymphomas, oligodendroglioma, esophageal carcinoma, osteosarcomas, ovarial carcinoma, pancreatic carcinoma, penile cancer, plasmocytoma, prostate cancer, pharyngeal cancer, rectal carcinoma, retinoblastoma, vaginal cancer, thyroid carcinoma, Schneeberger disease, esophageal cancer, spinal glioma, T-cell lymphoma (mycosis fungoides), thymoma, tube carcinoma, eye tumors, urethral cancer, urologic tumors, urothelial carcinoma, vulva cancer, wart appearance, soft tissue tumors, Wilm's tumor, cervical carcinoma and tongue cancer.

Preferably the concerned cancer is chosen from the group comprising bladder cancer, breast cancer, cancer of the central nervous system, colon cancer, stomach cancer, lung cancer, skin cancer, head and neck cancer, ovarian cancer, cervical cancer, glioblastomas, prostate cancer, testicular cancer, leukemia, liver cancer, kidney cancer and epithelial cancer types.

Also subject of the invention are further combined preparations of at least one of the afore-mentioned compounds according to the invention together with a cytostatic. Considered as cytostatics are alkylating agents, antibiotics with cytostatic properties, antimetabolic agents, alkaloids, podophyllotoxins, platinum containing compounds, taxanes, cytostatic active agents and monoclonal antibodies. Examples for these compound classes are for example cyclophosphamide, ifosfamide, trofosfamide, temozolomide, chlorambucil, melphalan, busulfan, treosulfan, thiotepa, estramustine, nimustine, carmustine, lomustine, dacarbazine, procarbazine, adriamycin (doxorubicin), epirubicin (4-epi-adriamycin), idarubicin, actinomycin D, daunorubicin, bleomycin, dactinomycin, mitomycin C, mitoxantrone, methotrexate, 5-fluorouracil, capecitabine, cytosine arabinoside, thioguanine, mercaptopurine, fludarabine, cladribine, gemcitabine, vincristine, vinblastine, vindesine, etoposide, teniposide, cisplatin, carboplatin, oxaliplatin, paclitaxel, docetaxel, hydroxycarbamide (hydroxyurea), imatinib, miltefosine, amsacrine, topotecan (topoisomerase-I inhibitor), pentostatin, bexarotene, tretinoin, asparaginase, trastuzumab (HERCEPTIN®), alemtuzumab (MABCAMPATH®), rituximab (MABTHERA®).

The present invention also comprises pharmaceutics, which contain one or more cysteine containing peptides according to invention and/or functional derivatives of these peptides. Especially preferred are pharmaceutics, which contain in addition at least one carbon suboxide derivative and/or one cytostatic and cytotoxic compound, respectively.

The cysteine containing peptides according to the invention can be used both as defense agents against pathogens and pharmaceutical active agents for the control of the infections and diseases caused by the pathogens. Especially possible is the use against diseases which are characterized by a chronic deficient immunoregulation, such as for example autoimmune diseases, cancer or AIDS. The cysteine containing peptides according to the invention can be utilized separately as single substances, but also as a mixture of several peptides or together with other already known active agents and substrate materials.

The combined preparations according to the invention as well as the pharmaceutical compositions according to the invention, which contain at least one peptide according to the invention, are produced in a known way using common solid or liquid substrates or diluents and commonly used pharmaceutical adjuvants according to the intended type of application with a suitable dosage. The preferred pharmaceutical compositions or preparations consist in a form which is suitable for oral administration or for inhalation. Such forms are for example tablets, film tablets, layer tablets, coated tablets, capsules, micro capsules, pills, granulates, powders, solutions, dispersions, suspensions, suppositories, emulsions, dispersions, gels, ointments, syrup or depot forms or inhalation solutions and inhalation powders, respectively. In addition the pharmaceutical compositions according to the invention comprise formulations such as layered tablets for the controlled and/or continuous release of the active agent as well as micro encapsulations as special application forms.

Such pharmaceutical compositions are inter alia suitable for the inhalation or the intravenous, intraperitoneal, intramuscular, subcutaneous, mucocutaneous, oral, rectal, transdermal, topical, intradermal, intragastrical, intracutaneous, intravaginal, intranasal, intrabuccal, percutaneous or sublingual application. Especially advantageous forms of application are oral administration, injection as well as inhalation.

Appropriate tablets can be obtained, for example, by mixing the applicable compound according to the invention and/or its salt with known adjuvants, for example inert diluents such as dextrose, sugar, sorbitol, mannite, polyvinylpyrrolidone, disintegrating agents such as corn starch or alginic acid, binding agents such as starch or gelatin, lubricants such as magnesium stearate or talcum and/or agents for producing a depot effect such as carboxyl polymethylene, carboxymethyl cellulose, cellulose acetate phthalate or polyvinyl acetate. The tablets may also consist of multiple layers.

Accordingly, pills can be produced by coating the cores produced in an analogous way as the tablets with agents, that are typically used in pill coatings, for example polyvinylpyrrolidone or shellac, gum arabic, talcum, titanium dioxide or sugar. The pill coating may also consist of multiple layers, whereas the adjuvants mentioned above for tablets can be used as well.

Solutions or suspensions with the active agent applicable according to the invention may further contain taste enhancing agents such as saccharin, cyclamate or sugar as well as aromatizers such as vanillin or orange extract. They may further contain suspending adjuvants such as sodium carboxymethyl cellulose or preservatives such as p-hydroxybenzoates. Capsules containing active agents can be produced, for example, by mixing the active agent with an inert substrate such as lactose or sorbitol, and encapsulating it in gelatin capsules.

Suitable suppositories can be produced, for example, by mixing with the substrates such as neutral fats or polyethylene glycol and derivatives thereof, respectively.

Such compositions are inter alia suitable for the inhalation or the intravenous, intraperitoneal, intramuscular, subcutaneous, mucocutaneous, oral, rectal, transdermal, topical, intradermal, intragastrical, intracutaneous, intravaginal, intranasal, intrabuccal, percutaneous or sublingual administration.

As pharmacologically acceptable substrates for example lactose, starch, sorbitol, sucrose, cellulose, magnesium stearate, dicalcium phosphate, calcium sulfate, talcum, mannite, ethyl alcohol and the like can be utilized. Powders as well as tablets can consist of 5 to 95% of such a substrate.

As binders can be used in addition starch, gelatin, natural sugars, natural as well as synthetic gums such as for example acacia gum or guar gum, sodium alginate, carboxymethyl cellulose, polyethylene glycol and waxes. As lubricants can serve boric acid, sodium benzoate, sodium acetate, sodium chloride, and the like.

Further disintegrating agents, coloring agents, flavoring agents and/or binders can be added to the pharmaceutical compositions.

Liquid compositions comprise solutions, suspensions, sprays and emulsions. For example injection solutions based on water or on water-propylene glycol for parenteral injections.

For the preparation of suppositories preferably low melting point waxes, fatty acid esters and glycerides are utilized.

Capsules are prepared for example from methyl cellulose, polyvinyl alcohols or denatured gelatin or starch.

As disintegrating agents can be used starch, sodium carboxymethyl starch, natural and synthetic gums such as for example carob flour, karaya, guar, tragacanth and agar, as well as cellulose derivatives such as methyl cellulose, sodium carboxymethyl cellulose, microcrystalline cellulose as well as alginates, clays and bentonites. These constituents can be utilized in amounts from 2 to 30% by weight.

As binders can be added sugars, starch from corn, rice or potatoes, natural gums such as acacia gum, gelatin, tragacanth, alginic acid, sodium alginate, ammonium calcium alginate, methyl cellulose, sodium carboxymethyl cellulose, hydroxypropyl methyl cellulose, polyvinylpyrrolidone, as well as inorganic compounds such as magnesium aluminum silicate. The binders can be added in amounts from 1 to 30% by weight.

As lubricants can be utilized stearates such as magnesium stearate, calcium stearate, potassium stearate, stearic acid, high melting point waxes, as well as water soluble lubricants such as sodium chloride, sodium benzoate, sodium acetate, sodium oleate, polyethylene glycol and amino acids such as leucine. Such lubricants can be used in amounts from 0.05 to 15% by weight.

A preferred application of the cysteine containing peptides according to the invention is in the support of the defense of biological organisms, especially plants, against bacterial, fungal, viral or other pathogens. The application can be carried out by administering the peptide into the nutrients/fluids incorporated by the plant or by applying the solution containing the peptide onto the surface of the plant leafs.

The present invention also comprises the genetic integration of gene sequences, which express a peptide according to the invention, into the genome of an organism menaced by a disease, preferably into the genome of plants. The increased resistance of the novel organism created by this genetic alteration offers a clearly more gentle protection for humans and the environment against pathogens than the chemical pesticides known up to know.

The peptides according to the invention can be utilized in a similar way for the preventive fortification of the defense of other, especially animal organisms, against pathogen infections of different types. By this way of application insects, nematodes and others carrying pathogens are successfully antagonized. Thereby the transfer and release, respectively, of the pathogens is prevented very efficiently and this takes place before they can exert their pathogenic effect.

Another application of the peptides according to the invention is carried out by application to a biologic, especially animal organism, already infected with a pathogen. Thereby the damaging consequences of bacterial, viral or other infections are neutralized or at least minimized. For this purpose the peptide or the mixture containing the peptide is utilized in that it causes together with the organisms own defenses a clearly more effective control of the pathogen.

The peptides according to the invention result in a significant reduction of the expression of some pro-inflammatory cytokines in humans and animals, especially of IL-2, IL-3, IL-4 and γ-IFN. Thus the peptides according the to invention are capable of significantly reducing the auto-aggressive processes targeted against self tissue, especially in the case of autoimmune diseases By stimulation of inhibitory cytokines, especially of TGF beta, the peptides according to the invention are capable of decreasing the activity of the primary human immune cells, which are pathologically over-activated in the case of autoimmune diseases. Especially promising experimental results were obtained in the case of topical application of the peptides according to invention in the case of skin diseases with autoimmune character, especially in the treatment of psoriasis.

By stimulating the production of the suppressively acting and potentially regulatory cytokine IL-10 the normal equilibrium between the pro- and anti-inflammatory cytokines, which is out of control in the case of autoimmune diseases and other chronic diseases, is reestablished by the peptides according to the invention.

The peptides according to the invention exert an efficient and partially selective inhibition on the propagation of malignant cancer cells. This could be confirmed by cell culture experiments.

The present invention also comprises pharmaceutical compositions and pharmaceutics, which contain as the effective portion a peptide according to the invention or a mixture of peptides according to the invention. The present invention further comprises pharmaceutical compositions and pharmaceutics, which contain a peptide according to the invention or a mixture of peptides according to the invention together with at least one already known active agent and/or together with pharmaceutically acceptable and suitable compounds and substrates.

The use of a peptide according to the invention together with the carbon suboxide derivatives referred to as MCS results in a clearly improved bioavailability and immunoregulatory effectiveness of the peptide, especially in the case of oncological applications (see examples).

For increasing the selectivity in the case of the control of malignant tumor cells the peptides according to the invention can be coupled with tumor-specific antigens. According to a preferred embodiment the peptide with the sequence HT-C1 is bound to the antibody, which was generated against human prostate carcinoma cells and isolated by affinity chromatography. The bonding is carried out by means of established coupling reagents such as carbodiimides, preferably with the water soluble 1-ethyl-3-(3-dimethylaminopropyl)-carbodiimide (EDAC).

Compared to the use of single peptides according to the invention the use of a mixture of the peptides according to the invention offers clear advantages. In comparison to the presence of a single agent a mixture of several active agents hampers the formation of pathogen resistance. The same advantages result in the case of both the biological defense through the transgenic expression of the peptide mixture and the control of disease through the administration of the peptide to the already diseased organism.

Thus the peptides according to the invention can be utilized in the above described ways as an active agent. In addition to the use of the single peptides according to the invention the peptides according to the invention are used as mixture of several peptides as well as together with other substances, especially together with carbon suboxide derivatives. To be considered as forms of administration are injections, a spray and a topical application.

The peptides according to the invention are used in the case of all of the application types in a 0.0001 to 10% solution, especially in a 0.01 to 1% solution, especially preferred in an about 0.2% solution. Especially preferred is the use of an aqueous peptide mixture. The treatment can be carried out for example by the daily administration of 3×10 ml of the aqueous peptide solution.

The peptides according to the invention can be administered to the humans, animals or plants to be treated as a pure compound or as a pharmaceutical composition, wherein they are administered in a therapeutically effective dosage in a mixture with substrates or diluents. Such therapeutically effective dose rates can be administered separately or in connection with other therapeutic compounds. In the case of the use for the treatment of cancer in this context come into consideration antiproliferative and antiangiogenic agents such as cytostatic or cytotoxic anti-tumor agents such as 5FU, cisplatin or also protein kinase inhibitors such as the Flk-1/KDR inhibitor CGP 79787, compounds of the class indolocarbazoles such as Gö7612, compounds of the class bisindolylmaleimides such as LY 333531, GF109203x, Ro 32-0432, Ro 31-8220, compounds of the class balanol derivatives such as SPC 100840, compounds of the class antisense oligodeoxynucleotides such as CGP 64128A and VEGF antisense oligonucleotide, compounds of the class of the alkyl lysophospholipids such as ET-18-OCH3, inhibitors of growth factor receptor activation such as anti-HER2/neu antibody, trastuzumab (HERCEPTIN®), inhibitors of growth factor receptor kinase activity such as compounds of the class phenylamino chinazolines such as PQ 153035, ZD 1839 and CP-358774, compounds of the class substituted pyrimidines comprising pyrido-, pyrrolo-, pyrazolo-, pyrimido- and phenylamino pyrimidines such as PD 158780, PD 166285, CGP 59326, CGP 60261 and CGP 62706, compounds of the class tyrphostines AG1478, RG 13022 and AG 825, compounds of the class lavendustins such as lavendustin A, compounds of the class dianilinophthalimides such as CGP54698, as well as compounds chosen from the group comprising inhibitors of Mitogen Activated Protein Kinase Kinase Kinase (MAP-KKK), inhibitors of Mitogen Activated Protein Kinase Kinase (MAPKK), inhibitors of Mitogen Activated Protein Kinase (MAPK) such as PD098059, U0126 or SB203580, interferon alpha, recombinant factor 4 for blood platelets, angiostatin or the poly-anionic compound suramin. The present invention also comprises the combination of the peptides according to the invention with one of the above indicated compounds.

Techniques for the formulation and administration of the peptides according to the invention can be found in "Remington's Pharmaceutical Sciences" Mack Publishing Co., Easton Pa. A composition, which comprises one of the peptides according to the invention, can be present in the form of a solution of the peptide according to the invention, in a liquid pharmaceutical substrate or in any other formulation such as tablets, pills, coated pills, capsules, gel, syrup, slurry, suspension and the like.

SHORT DESCRIPTION OF THE DRAWINGS

The invention shall be explained in more detail in the following on the basis of the embodiments in the context with the figures.

WAYS OF REALIZING THE INVENTION

Example 1

Extraction of a Peptide Mixture

About 10 kg of roughly milled root or rootstock of *Helleborus niger* (Ranunculaceae family) are treated for 6 hours with 50 l of a TBM/hexane mixture (1:1). The defatted and air dried plant material is extracted two times with 60 l of EtOH 50% for about 24 h under slight stirring at room temperature. The combined alcoholic-aqueous solutions are reduced in the vacuum rotary evaporator at 70° C. until dryness. The dry residue is treated three times with 3 l of 0.05 N hydrochloric acid, the resulting aqueous emulsions are combined and extracted successively with 10 l each of hexane, chloroform and TBM. The aqueous phase is reduced under vacuum to about 10 l of volume and the solution is treated with about 200 g of active carbon (2 hours). The filtrate is reduced under vacuum up to 1.0 l. The aqueous concentrate is adjusted by means of a 1 N HCl solution to pH value 1.2 and poured into a tenfold volume of cooled (10° C.) acetone under strong stirring. The white precipitate that is formed is separated from the supernatant by centrifugation and dried under vacuum. The dry precipitate is subsequently dissolved in a minimal amount of water and poured into an about tenfold volume of cooled acetone under stirring. This precipitating procedure is repeated once again, the resulting mixture of the cysteine containing peptides is dissolved in water and lyophilized.

Figure 1:
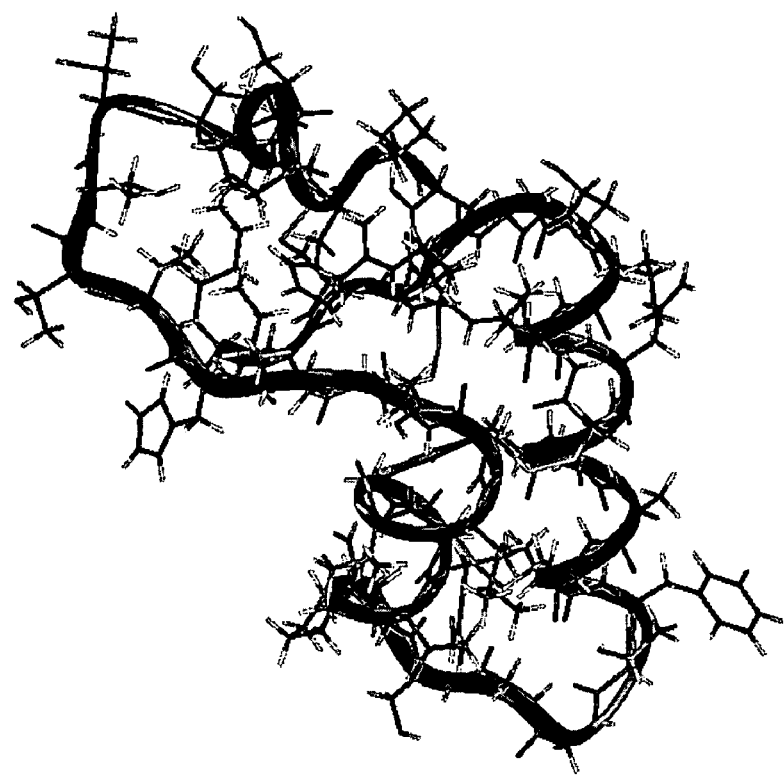
FIG. 1 shows the structure of the hellethionin HT-D.
Figure 2:
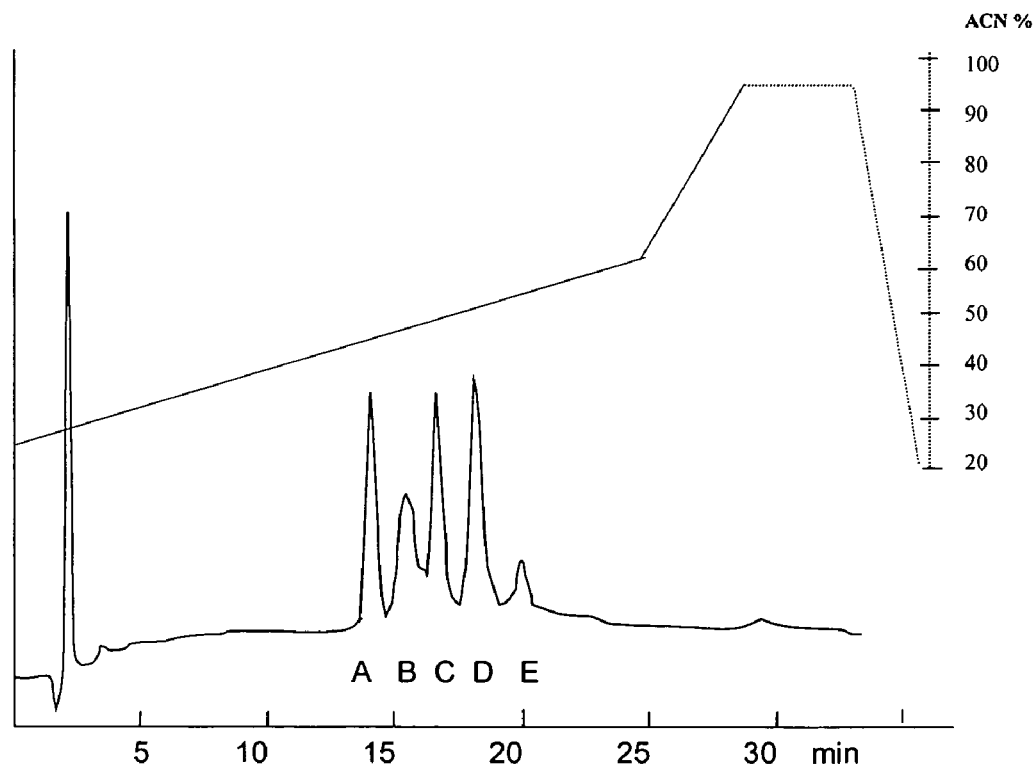
FIG. 2 shows a HPLC diagram of a hellethionin mixture; ACN % is the Acetonitrile %

The mixture of the peptides according to the invention is characterized by HPLC (FIG. 2). A Nucleosil 100-7, C-18 column (Macherey-Nagel Düren) with 250 mm length and 21 mm ID was used. At a flow rate of 3 ml/min and in a linear elution gradient of 20-50% of acetonitrile in 25 min the peptides according to invention elute as follows:

| | |
|---|---|
| Hellethionin-A | 14.4 min. |
| Hellethionin-B1 to hellethionin-B6 | 16.1 min. |
| Hellethionin-C | 16.9 min. |
| Hellethionin-D | 18.3 min. |
| Hellethionin-E1, hellethionin-E2 | 20.1 min. |

Example 2

Extraction of the Pure Peptide HT-D

About 1 kg of milled roots of the plant *Helleborus purpurascens* are extracted for 4 hours with 10 l of diluted acetic acid (5% in water) at 40° C. The filtered solution is reduced under vacuum up to 1 l. Afterwards about 400 g of ammonium sulphate is dissolved in the solution. The precipitate that is formed is separated by centrifugation, dissolved in a minimal amount of water and then added to a mixture of 3.6 l of acetone and 1.4 l of ethanol under strong stirring. The formation of the precipitate in the acetone/ethanol mixture is repeated two times and the resulting raw peptide mixture is dissolved in water and lyophilized.

Afterwards 5 g of the lyophilized raw mixture of the peptide from the species *Helleborus* is dissolved in 100 ml of 20% acetonitrile/water with 0.1% content of trifluoroacetic acid and separated into individual components by means of the preparative high pressure liquid chromatography (HPLC). For this purpose the sample solution is added in aliquot amounts on a Nucleosil 100-7, C-18 column (Macherey-Nagel Düren) with 250 mm length and 21 mm ID (internal diameter). The separation is carried out at a flow rate of 3 ml/min by means of a linear elution gradient of 20-50% acetonitrile in 30 minutes. The individual pure peptides are collected by means of a sample collector of the type FRAC-100 from Pharmacia-Biotech. The pure peptide HT-D is collected in the retention time interval of 17.9-18.7 min.

The testing of the purity of the isolated peptide hellethionin-D is carried out by analytic HPLC by means of a "Luna-CN" column from Phenomenex (Offenbach) with 200 mm length and 4 mm diameter using a linear gradient of 5-85% of acetonitrile in 40 minutes.

The $^1$H NMR spectrum of the pure hellethionin-D in water was correlated with the amino acid sequence determined through the Edman decomposition and the individual signals were assigned by means of Nuclear Overhauser Enhancement Spectroscopy (NOESY)- and Total Correlation Spectroscopy (TOCSY)-spectra. Table 1 illustrates the individual resonance signals for HT-D obtained through this correlation.

TABLE 1

$^1$H NMR signal assignments for hellethionin-D

| Position | Amino acid | H-N | H-C alpha | H-C beta | H-C gamma | H-C delta | others |
|---|---|---|---|---|---|---|---|
| 1 | Lys | | 3.72 | 1.36-1.47 | 0.83 | 1.1-1.03 | HE: 2.64 HZ: 7.17 |
| 2 | Ser | 8.52 | 4.65 | 3.41-2.96 | | | |
| 3 | Cys | 8.45 | 4.6 | 4.22-1.93 | | | |
| 4 | Cys | 9.47 | 4.9 | 2.60-2.14 | | | |
| 5 | Arg | 7.52 | 3.51 | 1.65 | 1.35-1.30 | 2.93-2.62 | H-E: 7.00 |
| 6 | Asn | 6.82 | 4.46 | 3.01 | 7.51-6.45 | | |
| 7 | Thr | 8.3 | 3.58 | 3.79 | 0.94 | | |
| 8 | Leu | 7.65 | 3.77 | 1.38-1.29 | 0.57-0.61 | | |
| 9 | Ala | 8.02 | 4.07 | 1.52 | | | |
| 10 | Arg | 7.68 | 4.16 | 1.92-1.36 | 1.59 | 3.06-3.30 | HE: 8.07; HH: 6.10 |
| 11 | Asn | 8.16 | 4.21 | 2.64-2.60 | 6.7-7.29 | | |
| 12 | Cys | 8.15 | 3.89 | 3.58-2.72 | | | |
| 13 | Tyr | 8.74 | 3.36 | 3.06-2.89 | | | HE: 6.40 |
| 14 | Asn | 8.55 | 4 | 2.62-2.52 | 7.6 | | |
| 15 | Ala | 7.63 | 3.93 | 1.19 | | | |
| 16 | Cys | 7.98 | 3.8 | 2.83-2.78 | | | |
| 17 | Arg | 8.26 | 3.79 | 1.48-1.37 | 0.88-0.62 | 2.72-2.15 | HE: 6.72; HH: 6.8-6.3 |
| 18 | Phe | 8 | 4.01 | 3.07-2.94 | | | HD; HE; HZ: 7.01-6.91 |
| 19 | Thr | 7.24 | 3.94 | 4.27 | 1.06 | | |
| 20 | Gly | 7.24 | 4.04-3.30 | | | | |
| 21 | Gly | 7.88 | 3.73-3.12 | | | | |
| 22 | Ser | 8.45 | 4.03 | 3.90-3.74 | | | |
| 23 | Gln | 9.01 | 3.76 | 1.84-1.73 | 2.20-1.95 | 1.95 | HE: 7.1-6.58 |
| 24 | Pr | | 4.05 | 1.99-1.56 | 1.78-1.65 | 3.54-3.39 | |
| 25 | Thr | 7.1 | 3.55 | 3.8 | 0.84 | | |
| 26 | Cys | 8.4 | 4.28 | 2.29-2.16 | | | |
| 27 | Gly | 8.42 | 3.83-3.45 | | | | |
| 28 | Ile | 7.44 | 3.66 | 1.67 | 1.41-1.01 | 0.56 | |
| 29 | Leu | 7.81 | 3.81 | 1.54-1.45 | 1.28 | 0.57 | |
| 30 | Cys | 7.4 | 4.51 | 3.54-2.65 | | | |
| 31 | Asp | 7.7 | 4.27 | 3.36-2.62 | | | |
| 32 | Cys | 8.84 | 5.24 | 2.64-1.79 | | | |
| 33 | Ile | 8.64 | 4.25 | 1.4 | 0.57-0.7 | −0.01 | |
| 34 | His | 8.52 | 4.82 | 2.73-2.69 | 8.53 | | |
| 35 | Val | 7.96 | 4.44 | 1.99 | 0.44-0.39 | | |
| 36 | Thr | 8.54 | 4.15 | 4.21 | 0.89 | | |
| 37 | Thr | 6.65 | 4.17 | 4.31 | 0.91 | | |
| 38 | Thr | 8.22 | 3.82 | 4.02 | 0.93 | | |
| 39 | Thr | 6.78 | 4.16 | 3.79 | 0.82 | | |
| 40 | Cys | 8.57 | 4.59 | 3.55-2.14 | | | |
| 41 | Pro | | 4.29 | 1.98-1.84 | 1.5 | 3.51-3.30 | |
| 42 | Ser | 8.55 | 3.94 | 3.71-3.59 | | | |
| 43 | Ser | 7.62 | 3.87 | 3.76-3.65 | | | |
| 44 | His | 7.41 | 4.37 | 2.21-2.01 | 6.72 | | HE: 8.44 |
| 45 | Pro | | 4 | 1.66 | 1.66 | 3.42-3.07 | |
| 46 | Ser | 7.78 | 4.04 | 3.42-2.56 | | | |

Example 3

Effect of the Peptide HT-A on the Cytokine Production of Primary Human Immune Cells The effect of the peptide HT-A on the cytokine production of primary human immune cells was determined through the measurement of the concentration of cytokines in lymphocyte cultures obtained from human blood. Dosages of 4-200 µg/ml of the hellethionins were used, which were obtained by adding the calculated amounts in the form of a stock solution. The concentration of individual cytokines in the treated and control samples is determined by means of the commercially available "Quantikine" ELISA plates from R&D Biosystems, Minneapolis, USA. The results were compared with control samples, i.e. with the lymphocyte culture without addition of the peptide.

In the case of the lymphocyte cultures (4 million cells per ml) treated with 4 µg and 200 µg of the peptide HT-A, respectively, the following cytokine (and cytokine receptor) concentrations [pg/ml] were obtained in comparison with the control sample (without peptide):

| Cytokine/peptide | Control [without peptide] | HT-A [4 µg/ml] | HT-A [200 µg/ml] |
|---|---|---|---|
| inhibited | | | |
| IL-2 [pg/ml] | 9.390 | 1.940 | 1.855 |
| IL-3 [pg/ml] | 41 | 26 | 8 |
| IL-4 [pg/ml] | 34 | 19 | 12 |
| γ-IFN [pg/ml] | 11.605 | 7.454 | 7.504 |
| IL-6R [pg/ml] | 171 | 100 | 65 |
| stimulated | | | |
| IL-10 | 69 | 288 | 12 |
| IL-2R | 44 | 30 | 67 |
| TGF-β2 | 9 | 105 | 45 |
| not influenced | | | |
| IL-6 | 1.095 | 1.100 | 1.130 |
| IL-1RA | 2.170 | 2.204 | 2.467 |
| TNF-α | 2.105 | 1.860 | 2.085 |

These data show, that the peptide HT-A is inhibiting the expression of several pro-inflammatory cytokines such as for example IL-2, IL-3, IL-4 and γ-IFN. By suppressing the production of these cytokines the use of the peptide results in the desired reduction of the harmful auto-aggressive processes of autoimmune diseases.

Furthermore the peptide HT-A shows a stimulation of the cytokines acting suppressively such as IL-10 and TGF-β2. Interestingly the stimulation of these cytokines in the case of a low peptide concentration (4 µg/ml) is clearly more intense than in the case of a higher dosage (200 µg/ml). It is assumed, that in the case of a higher peptide concentration the non-specific cellular toxicity of the peptide overlaps the stimulation observed in the case of lower dose rates.

The tested peptide HT-A shows no significant influence on the production of some cytokines such as IL-6 or TNF-α and on the expression of the IL-1 receptor.

Example 4

Effect of the Peptide HT-C on the Proliferation of Human Cancer Cells

Figure 3:
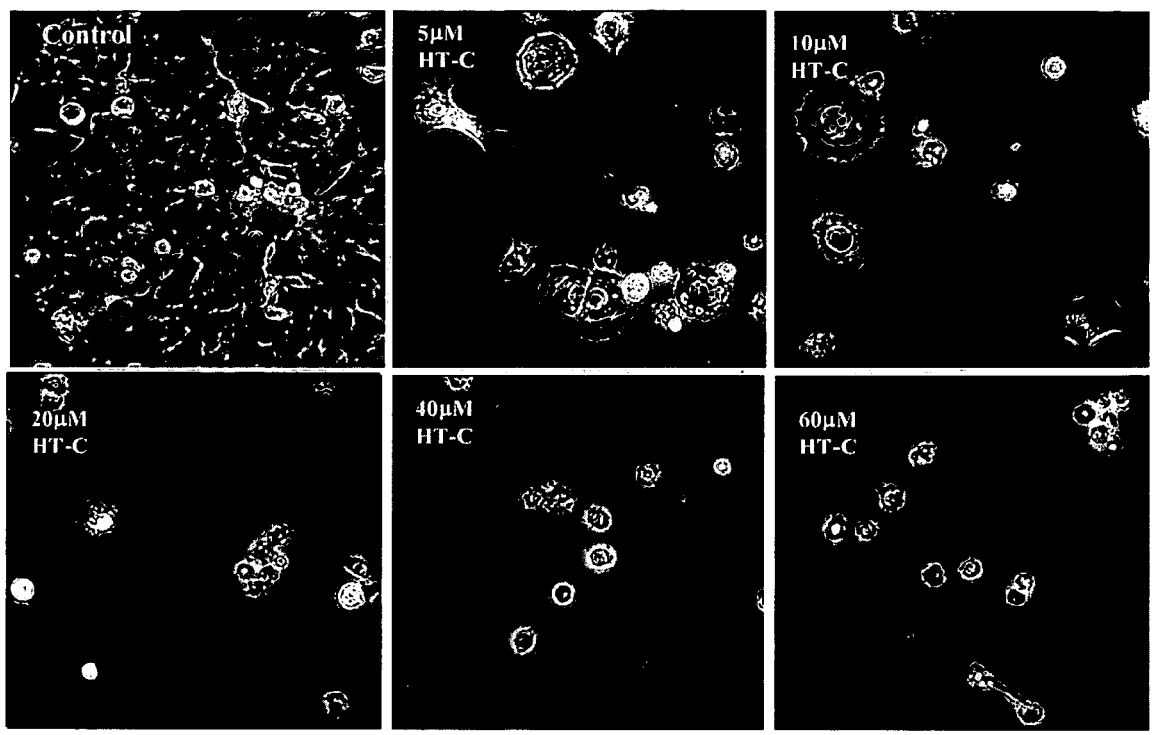
FIG. 3 shows the effect of different concentrations of the hellethionin HT-C on breast cancer cells of the type MCF-7.

The investigations were carried out with the breast cancer cell culture line MCF-7. A cell culture line from non differentiated breast epithelial cells of the type MCF-10A served as a comparison. The corresponding cells (about $10^5$/ml of sample) were initially stimulated in the standard DMEM culturing medium. After 24 hours the peptide HT-C was added and concentrations between 0.2 and 400 µg/ml were adjusted in this way. The examination of the alterations caused by the peptide was carried out at intervals of 24 hours during a time period of up to 6 days. The peptide HT-C already causes at low concentrations, namely already from 2 µg/ml, a very clear inhibition of the propagation of the MFC-7 cells (FIG. 3).

The peptide HT-C had a significantly minor inhibitory effect on the propagation of the non malignant epithelial cells of the type MFC-10 under the same conditions.

Example 5

Effect of the Peptide Mixtures on Tumour Development in Mice

In this study the effect of the peptides in mixture according to the invention was investigated on tumour development in the female with WAZ-2T cells inoculated mice of the type BALB/c with a body weight of 20-24 g. Initially the pathogenity of the cell strain was determined through the inoculation of an increasing dose rate of 0-$10^6$ tumour cells in the right breast fat pad of the animals (12 mice/dose rate). This pre-experiment showed, that the use of a dose rate of $2.5 \times 10^3$ tumour cells resulted in a tumour incidence of 66.7%, i.e. a palpable tumour developed in two of three mice. The diameter of the tumour was measured daily and corrected with a value of 0.1 cm for the skin thickness of the animal. The volume was calculated assuming a spherical shape of the tumour. The mice were sacrificed on day 120 or earlier, when the tumour had reached a diameter of more than 1.8 cm. The 80 animals were grouped in four groups (I to IV) with 20 mice each. On day zero all of the animals were inoculated with a suspension of $2.5 \times 10^3$ tumour cells.

The animals of the group I (control group) received their normal food without addition of the peptide mixture. In the case of animals reacting positively The development of the tumour was measurable from the fourth week after the inoculation. On day 50 after the inoculation a well measurable tumour had developed in the case of a total of 14 animals of this group. Thus the tumour incidence on day 50 was 70%. The average volume of the tumour in the positive animals was determined as follows:

| Day 50 | 0.81 cm³ |
|---|---|
| Day 60 | 1.23 cm³ |
| Day 70 | 1.74 cm³ |

The animals of group 11 received from the first day of the inoculation daily 0.4 µg of the peptide mixture according to the invention added to their food. On day 50 after the inoculation a palpable tumour was well measurable only in the case of 4 animals. Thus the tumour incidence on day 50 was 25%. The average volume of the tumour in the positive animals was determined as follows:

| Day 50 | 0.32 cm³ |
|---|---|
| Day 60 | 0.57 cm³ |
| Day 70 | 0.71 cm³ |

In the case of the animals of group III the treatment with the peptide mixture was started only from the 7$^{th}$ day after the inoculation. A daily dose rate of 0.4 µg of peptide mixture per animal was added to the food. On day 50 after the inoculation a palpable tumour was well identifiable in the case of a total of 9 animals. Thus the tumour incidence on day 50 was 45%. The average volume of the tumour in the positive animals was determined as follows:

| | |
|---|---|
| Day 50 | 0.48 cm$^3$ |
| Day 60 | 0.77 cm$^3$ |
| Day 70 | 0.93 cm$^3$ |

Thus the peptides according to invention cause a significant inhibition of the malignant disease rate of the animals and a regression of the development of tumour.

Example 6

Effect of the Peptides on Murine Peritoneal Macrophages

Murine peritoneal macrophages extracted from CD1 mice were used. A peritoneal flushing was carried out using 5 ml of PBS. After three washing processes with RPMI 1640 the cells were put into a 96-well culturing plate with a concentration of 1×10$^6$ cells/ml (200 µl/well) in 10% FCS-RPMI 1640 medium and kept for 24 hours. After the incubation the cells were washed three times with RPMI 1640 and resuspended in 10% FCS-RPMI 1640 medium (100 µl/well) in the absence (non stimulated) or in the presence (stimulated) of different stimulants. After 24 hours of incubation NO, IL-10 and TNF-α were measured in the culture supernatant.

| Sample | NO (µM) | TNF-α (pg/ml) | IL-10 (pg/ml) | Survival rate (%) |
|---|---|---|---|---|
| Control | 1.1 | 0 | 0 | 100 |
| HT-C 5 µg/ml | 0.7 | 244 | 6 | 80.3 |
| HT-C 100 µg/ml | 0.8 | 312 | 26 | 10.7 |
| HT-D 5 µg/ml | 0.8 | 18 | 0 | 87.6 |
| HT-D 100 µg/ml | 1.3 | 0 | 0 | 42.8 |

The peptide HT-C shows a clearly stronger cytotoxic effect than HT-D against the peritoneal macrophages from mice investigated herein. The tested peptides do not induce NO in the murine peritoneal macrophages.

Example 7

Effect of the Individual Peptides and in Mixture with Carbon Suboxide Compound (MCS-18) on Cancer Cells of the Line COLO-205

Methods:

Cell line: Colon cancer cell line: Colo 205 (ATCC Nr. CCL-222), organism: *homo sapiens*, literature: Cancer Res., 38, 1345-1355, 1978. PNAS, 99, 10718-10723, 2002.

After adherence of the cells (incubation 24 h, cell amount 1×10$^4$ cells per batch), the cells were treated for 24 h with MCS and/or peptides (Hellethionin C (CZT), Hellethionin D (DZT)) and afterwards the percentage of living cells was measured by MTT test.

Cell line: lung carcinoma cell line: A549 (ATCC No. CCL-185™), organism: *homo sapiens*, literature: Giard D J, et al. J. Natl. Cancer Inst. 51: 1417-1423, 1973.

After adherence of the cells (incubation 24 h, cell amount 5×10$^3$ cells per batch), the cells were treated for 72 h with MCS and/or peptides (CZT, DZT) and afterwards the percentage of living cells was measured by AlamarBlue test.

MTT-Test:

The MTT cell growth test was carried out according to Alley et. al. (M. C. Alley et al., Proc. Am. Assoc. Cancer Res., 27:389, 1986; M. C. Alley et al., Cancer Res. 48:589-601, 1988). The finale concentration of 3-(4,5-dimethylthiazol-2-yl)-2,5-diphenyltetrazoliumbromide was 0.4 mg/ml.

AlamarBlue™ cell growth test was carried out according to the specifications of the manufacturer (Serotec, Oxford, England, www.serotc.com).

Result:

As shown in table 2 the growth of the Colo 205 cells is already strongly inhibited after 24 hours at the concentration of 100 µg/ml in the presence of the peptides CZT and DZT. The amount of the living cells is only about 50%. When the substance MCS 18 is added in addition to the peptide CZT, a still improved inhibiting effect of the peptide can be observed. MCS 18 itself has at 100 µg/ml no inhibiting effect on the growth of the Colo 205 cells at all (table 3). Hence the combination of CZT peptide and MCS can result in an increased anti tumour activity in the case of colon cancer.

Figure 4:
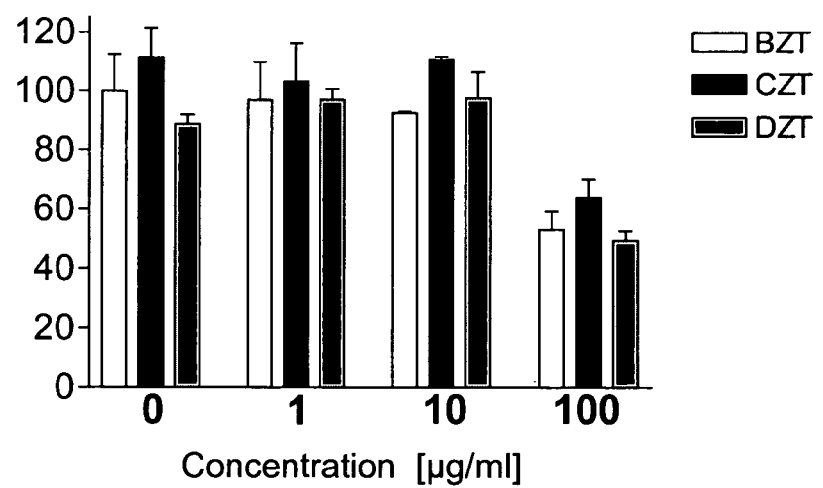
FIG. 4 shows the inhibitory effect of different concentrations of the peptides BZT, CZT and DZT on the growth of lung carcinoma cell line A549

The peptides BZT (referring to the native and naturally occurring mixture of Hellethionins B1, B2 and B3 in a ratio of about 1:1:1), CZT and DZT were also able to inhibit the growth of lung carcinoma cell lines at a concentration of 100 µg/ml (see FIG. 4). Only about 50% of living cells could be determined after 72 h.

TABLE 2

| Substance | Concentration in [µg/ml] | Living Colo 205 cells in [%] |
|---|---|---|
| — | — | 100 |
| CZT peptide | 50 | 92.15 |
| CZT peptide | 100 | 48.36 |
| DZT peptide | 50 | 92.15 |
| DZT peptide | 100 | 58.66 |

TABLE 3

| Substance | Concentration in [µg/ml] | Living Colo 205 cells in [%] |
|---|---|---|
| — | — | 100 |
| MCS 18 | 100 | 100 |
| CZT peptide | 50 | 92.15 |
| CZT peptide +MCS18 | 50 100 | 66.66 |

The invention claimed is:

1. An isolated cysteine containing peptide comprising:

KSCCRNTLGRNCYNGCRFTGGSQPTCGR-LCDCIHVTTTTCPSSHPS (SEQ ID NO: 1) (hellethionin-A), KSCCRNTLGRNCYNACRFTGGSQPTCGR-LCDCIHVTTTTCPSSHPS (SEQ ID NO: 2) (hellethionin-B1), KSCCRNTLARNCYNACRFTGGSQPTCGR-LCDCIHVTTTTCPSSHPS (SEQ ID NO: 3) (hellethionin-B2), KSCCRNTLGRNCYNACRLPGTPQPT-CATLCDCIHVTTPTCPSSHPR (SEQ ID NO: 4) (hellethionin-B3), KSCCRNTLARNCYNACRFTGTSQPYCAR-LCDCIHVTTPTCPSSHPR (SEQ ID NO: 5) (hellethionin-B4), KSCCRNTLARNCYNACRFTGGSQPT-CATLCDCIHVTTPTCPSSHPR (SEQ ID NO: 6) (hellethionin-B5), KSCCRNTLARNCYNVCRFGGGSQAY-CARFCDCIHVTTSTCPSSHPS (SEQ ID NO: 7) (hellethionin-B6)

KSCCRNTLGRNCYNACRLTGTSQAT-CATLCDCIHVTATTCRPPYPS (SEQ ID NO: 8) (hellethionin-C), KSCCRNTLARNCYNACR-FTGGSQPTCGILCDCIHVTTTTCPSSHPS (SEQ ID NO: 9) (hellethionin-D), KSCCRNTLGRNCYAACRLTGLFSQEQ-CARLCDCITVTTPTPCPRTHPS (SEQ ID NO: 10) (hellethionin-E1), or KSCCRNTLGRNCYAACRLTGTFSQEQ-CARLCDCITVTTPTPCPRTHPS (SEQ ID NO: 11) (hellethionin-E2).

2. Ester derivatives, amide derivatives, halogen derivatives and methyl derivatives of the isolated cysteine peptides according to claim 1.

3. A pharmaceutical composition comprising one or more isolated peptides according to claim 1 or pharmaceutically acceptable salt of said peptides or a mixture of the isolated peptides according to claim 1.

4. Pharmaceutical composition according to claim 3, further comprising at least one carbon suboxide derivative.

5. Pharmaceutical composition according to claim 4, further comprising at least one cytostatically or cytotoxically active compound.

6. Pharmaceutical composition according to claim 3, further comprising at least one cytostatically or cytotoxically active compound.

7. A method for extracting the cysteine containing peptide according to claim 1 comprising defatting a *helleborus* plant material using a non-polar solvent and extracting said peptide from the defatted material.

8. A method according to claim 7, wherein the non-polar solvent is tert-butyl methyl ether.

9. A method for production of the cysteine containing peptides according to claim 1 by a recombinant method.

10. A method for synthetic production of the cysteine containing peptide according to claim 1 by peptide synthesis.

* * * * *